(12) United States Patent
Zitzmann et al.

(10) Patent No.: US 7,256,005 B2
(45) Date of Patent: Aug. 14, 2007

(54) METHODS FOR IDENTIFYING IMINOSUGAR DERIVATIVES THAT INHIBIT HCV P7 ION CHANNEL ACTIVITY

(75) Inventors: Nicole Zitzmann, Odendort (DE); Raymond Allen Dwek Frs, Oxford (GB)

(73) Assignee: The Chancellor, Masters and Scholars of the University of Oxford, Oxford (GB)

( * ) Notice: Subject to any disclaimer, the term of this patent is extended or adjusted under 35 U.S.C. 154(b) by 230 days.

(21) Appl. No.: 10/669,175

(22) Filed: Sep. 23, 2003

(65) Prior Publication Data
US 2004/0110795 A1 Jun. 10, 2004

Related U.S. Application Data

(63) Continuation-in-part of application No. 10/031,145, filed as application No. PCT/US00/21732 on Aug. 10, 2000.

(60) Provisional application No. 60/412,560, filed on Sep. 23, 2002, provisional application No. 60/198,621, filed on Apr. 20, 2000, provisional application No. 60/148,101, filed on Aug. 10, 1999.

(51) Int. Cl.
    G01N 33/35      (2006.01)
    C12N 7/04       (2006.01)
(52) U.S. Cl. ..................................... 435/7.2; 435/235.1
(58) Field of Classification Search .................... None
     See application file for complete search history.

(56) References Cited

U.S. PATENT DOCUMENTS

| | | |
|---|---|---|
| 4,246,345 A | 1/1981 | Kinast et al. |
| 4,266,025 A | 5/1981 | Kinast et al. |
| 4,405,714 A | 9/1983 | Kinast et al. |
| 4,806,650 A | 2/1989 | Schroder et al. |
| 4,861,892 A | 8/1989 | Fleet |
| 4,894,388 A | 1/1990 | Fleet |
| 4,910,310 A | 3/1990 | Campbell et al. |
| 4,944,572 A | 7/1990 | Young |
| 4,996,329 A | 2/1991 | Fleet et al. |
| 5,011,929 A | 4/1991 | Fleet et al. |
| 5,013,842 A | 5/1991 | Fleet et al. |
| 5,017,704 A | 5/1991 | Fleet et al. |
| 5,043,273 A | 8/1991 | Scudder et al. |
| 5,100,797 A | 3/1992 | Fleet et al. |
| 5,200,523 A | 4/1993 | Fleet |
| 5,286,877 A | 2/1994 | Behling et al. |
| 5,310,745 A | 5/1994 | Partis et al. |
| 5,580,884 A | 12/1996 | Platt et al. |
| 5,622,972 A | 4/1997 | Bryant et al. |
| 6,291,657 B1 | 9/2001 | Platt et al. |
| 6,355,413 B1 | 3/2002 | Gage et al. |

2006/0252918 A1* 11/2006 Rowlands et al. .......... 530/350

FOREIGN PATENT DOCUMENTS

| | | |
|---|---|---|
| EP | 445098 A2 | 2/1991 |
| WO | WO 98/35685 A1 | 8/1998 |
| WO | WO 99/24401 A1 | 5/1999 |
| WO | WO 00/47198 A2 | 8/2000 |
| WO | WO 01/10429 A2 | 2/2001 |
| WO | WO 01/60366 A1 | 8/2001 |
| WO | WO 2004/005333 A1 * | 1/2004 |

OTHER PUBLICATIONS

Sakai et al. PNAS (2003) vol. 100, No. 20, 11646-11651.*
De Francesco, R. "Biochemical and immunologic properties of the nonstructural proteins of the hepatitis C virus: implications for development of antiviral agents and vaccines" Semin. Liver Dis. 2000; 20 (1): 69-83.*
Griffin, S.D.C. "A conserved basic loop in hepatitis C virus p7 protein is required for amantadine-sensitive ion channel activity.in mammalian cells but is dispensible for localization in mitochondria" Journ. Gen. Virol. 2004; 85: 451-461.*
Carrere-Kremer, S. "Subcellular localization and Topology of the p7 Polypeptide of Hepatitis C Virus" J. Virol. Apr. 2002; 76 (8): 3720-3730.*
Griffin, S.D.C. "The protein of hepatitis C virus forms an ion channel that is blocked by the antiviral drug, Amantadine" FEBS Letters 2003; 535: 34-38.*
Rokitskaya, Antonenko, Kotova, Anastasiadis and Separovic, 2000, Biochemistry, 39, 13053-13058. Effect of Avidin on Channel Kinetics of Biotinylated Gramicidin.*
Swartz and MacKinnon, 1995, Neuron, 4, 941-9. An inhibitor of the Kv2.1 potassium channel isolated from the venom of a Chilean tarantula.*
Smith JP, 1997, Dig Dis Sci, 42(8), 1681-7. Treatment of chronic hepatitis C with amantadine.*
Griffin et al (2003) FEBS Letters. 535: 34-38.*
Di Bisceglie, Adrian M., "Hepatitis C and Hepatocellular Carcinoma," Hepatology vol. 26, No. 3, Suppl. 1, Sep. 1997, pp. 345-350.
Egger et al., "Expression of Hepatitis C Virus Proteins Induces Distinct Membrane Alterations Including a Candidate Viral Replication Complex", *Journal of Virology, American Society for Microbiology*, vol. 76, No. 12, Jun. 2002, pp. 5974-5984.

(Continued)

*Primary Examiner*—Bruce R. Campell
*Assistant Examiner*—Michelle Horning
(74) *Attorney, Agent, or Firm*—Foley & Lardner LLP

(57) ABSTRACT

Disclosed are methods for screening that may be used to identify an inhibitor of HCV p7 protein. The methods may include incorporating an HCV p7 protein into a membrane to create an HCV p7-containing membrane that has an increased permeability relative to a membrane that does not contain HCV p7 protein. The HCV p7 protein may be contacted with a test compound, and the permeability of this HCV p7-containing membrane then may be compared to an HCV p7-containing membrane in which the HCV p7 protein has not been contacted with the test compound. The inhibitor of HCV p7 protein may be identified by observing a decrease in the permeability of the HCV p7-containing membrane in which the HCV p7 protein has been contacted with the test compound.

19 Claims, 8 Drawing Sheets

OTHER PUBLICATIONS

Annex to Form PCT/ISA/206, Communication Relating To The Results Of The Partial International Search, date of mailing Sep. 13, 2004, 2 pages.

Bergeron et al., "Calnexin: a membrane-bound chaperone of the endoplasmic reticulum," TIBS Mar. 19, 1994, Elsevier Scient Ltd. 0968-0004/94 pp. 124-128.

Branza-Nichita et al., "Antiviral of N-Butyledeoxynojirimycin against Bovine Viral Diarrhea Virus Coorelates with Misfolding of E2 Envelope Proteins and Impairment of Their Association into E1-E2 Heterodimers," (2001) J. Virol. 75(8), pp. 3527-36.

Carrere-Kremer et al., Subcellular Localization and Topology of the p7 Polypeptide of Hepatitis C Virus, (2002) J. Virol. 76(8), pp. 3720-30.

Choukhi et al., Involvement of Endoplasmic Reticulum Chaperones in the Folding of Hepatitus C Virus Glycoproteins, (1998) J. Virol., 72(5), pp. 3851-8.

Courageot et al., "α-Glucosidase Inhibitors Reduce Dengue Virus Production by Affecting the Initial Steps of Virion Morphogenesis in the Endoplasmic Reticulum," (2000) J. Virol., 74(1): pp. 564-72.

Duff et al., "The Transmembrane Domain of Influenza A M2 Protein Forms Amantadine-Sensitive Proton Channels in Planar Lipid Bilayers," Virology 190, pp. 485-489 (1992) 0042-6822/92 Copyright 1992 by Academic Press, Inc.

Durantel et al., "Study of the Mechanism of Antiviral Action of Iminosugar Derivatives against Bovine Viral Diarrhea Virus," (2001) J. Virol. 75(19): pp. 8987-98.

Dwek, et al., "Targeting Glycosylation as a Therapeutic Approach," Nature Reviews/Drug Discovery, vol. 1 Jan. 2002, pp. 65-75. Glycobiology Institute, Dept. of Biochemistry, University of Oxford, Oxford OX1 3QU, UK.

Fischer et al., "Amantadine blocks channel activity of the transmembrane segment of the NB protein from influenza B," Eur. Biophys J. (2001) 3-: pp. 416-420, DOI 10.1007/s00240100157.

Griffin et al., "The p7 protein of hepatitis C virus forms an ion channel that is blocked by the antiviral drug, Amantadine," FEBS Letters 535 (2003) pp. 34-38, Elsevier Science B.V. on behalf of the Federation of European Biochemical Societies.

Harada et al., "E2-p7 Region of the Bovine Viral Diarrhea Virus Polyprotein: Processing and Functional Studies," (2000) J. Virol. 74(20): pp. 9498-506.

Hay et al., "The molecular basis of the specific anti-influenza action of amantadine," EMBO Journal, vol. 4 No. 11 pp. 3021-3024, 1985. Oxford, England.

Lin et al., "Processing in the Hepatitis C Virus E2-NS2 Region: Identification of p7 and Two Distinct E2-Specific Products with Different C Termini," (1994) J. Virol. 68(8): pp. 5063-73.

Lohmann et al., "Replication of Subgenomic Hepatitis C Virus RNAs in a Hepatoma Cell Line," (1999) Science, 285(5424) pp. 110-3.

Mehta et al., "α-Glucosidase inhibitors as potential broad based anti-viral agents," FEBS Lett. Jun. 1998 23;430(1-2): pp. 17-22.

Mizushima et al., "Two Hepatitis C Virus Glycoprotein E2 Products with Different C Termini," (1994) J. Virol. 68(10): pp. 6215-22.

Montal et al., "Formation of Bimolecular Membranes from Lipid Monolayers and a Study of Their Electrical Properties," Proc. Nat. Acad. Sci. USA 69 (1972) pp. 3561-3566.

Pavlovic et al., "The hepatitis C virus p7 protein forms an ion channel that is inhibited by long-alkyl-chain iminosugar derivatives," PNAS May 13, 2003; 100(10): pp. 6104-8.

Peterson et al., "Transient, Lectin-like Association of Calreticulin with Folding Intermediates of Cellular and Viral Glycoproteins," Molecular Biology of the Cell, vol. 6, pp. 1173-1184, Sep. 1995 by The American Society for Cell Biology.

Pietschmann et al., "Characterization of Cell Lines Carrying Self-Replicating Hepatitis C Virus RNAs," (2001) J. Virol. 75(3): pp. 1252-64.

Reed et al., "Overview of Hepatitis C Virus Genome Structure, Polyprotein Processing, and Protein Properties," Department of Molecular Microbiology, Washington University School of Medicine, St. Louis, MO, pp. 55-84.

Sunstrom, et al., "Ion Channels Formed by NB, an Influenza B Virus Protein," J. Membrane Biol. 150, pp. 127-132 (1996).

Wu et al., "Antiviral Effects of an Iminosugar Derivative on Flavivirus Infections," (2002) J. Virol., 76(8): pp. 3596-604.

Xu et al., "Synthesis of a novel hepatitis C virus protein by ribosomal frameshift," (2001) The EMBO Journal 20(14): pp. 3840-8.

Zitzmann et al., "Imino sugars inhibit the formation and secretion of bovine viral diarrhea virus, a pestivirus model of hepatitis C virus: Implications for the development of broad spectrum anti-hepatitis virus agents," (2001) Proc. Natl. Acad. Sci. USA, Oct. 12, (21): pp. 11878-82.

* cited by examiner

SEQUENCE LISTING

```
<160> NUMBER OF SEQ ID NOS: 6

<210> SEQ ID NO 1
<211> LENGTH: 63
<212> TYPE: PRT
<213> ORGANISM: Artificial Sequence
<220> FEATURE:
<223> OTHER INFORMATION: Description of Artificial Sequence: Synthetic
      consensus amino acid sequence for HCV p7

<400> SEQUENCE: 1

Ala Leu Glu Asn Leu Val Val Leu Asn Ala Ala Ser Ala Ala Gly Thr
  1               5                  10                  15

His Gly Ile Leu Trp Phe Leu Val Phe Phe Cys Ala Ala Trp Tyr Val
             20                  25                  30

Lys Gly Arg Leu Val Pro Gly Ala Thr Tyr Ser Leu Leu Gly Leu Trp
         35                  40                  45

Pro Leu Leu Leu Leu Leu Leu Ala Leu Pro Gln Arg Ala Tyr Ala
```

-continued

```
            50                 55                 60

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aagcgcccat ggctttggag aacctcgtaa tac                              33

<210> SEQ ID NO 3
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
attgaattct tagtgatggt gatggtgatg gtggtggtat gcccgctgag gcaac      55

<210> SEQ ID NO 4
<211> LENGTH: 63
<212> TYPE: PRT
<213> ORGANISM: Hepatitis C virus

<400> SEQUENCE: 4

Ala Leu Glu Asn Leu Val Ile Leu Asn Ala Ala Ser Leu Ala Gly Thr
 1               5                  10                  15

His Gly Leu Val Ser Phe Leu Val Phe Phe Cys Phe Ala Trp Tyr Leu
            20                  25                  30

Lys Gly Arg Trp Val Pro Gly Ala Val Tyr Ala Leu Tyr Gly Met Trp
        35                  40                  45

Pro Leu Leu Leu Leu Leu Leu Ala Leu Pro Gln Arg Ala Tyr Ala
    50                  55                  60

<210> SEQ ID NO 5
<211> LENGTH: 33
<212> TYPE: PRT
<213> ORGANISM: Hepatitis C virus

<400> SEQUENCE: 5

Ala Leu Glu Asn Leu Val Ile Leu Asn Ala Ala Ser Leu Ala Gly Thr
 1               5                  10                  15

His Gly Leu Val Ser Phe Leu Val Phe Phe Cys Phe Ala Trp Tyr Leu
            20                  25                  30

Lys

<210> SEQ ID NO 6
<211> LENGTH: 30
<212> TYPE: PRT
<213> ORGANISM: Hepatitis C virus

<400> SEQUENCE: 6

Gly Arg Trp Val Pro Gly Ala Val Tyr Ala Leu Tyr Gly Met Trp Pro
 1               5                  10                  15

Leu Leu Leu Leu Leu Leu Ala Leu Pro Gln Arg Ala Tyr Ala
            20                  25                  30
```

METHODS FOR IDENTIFYING IMINOSUGAR DERIVATIVES THAT INHIBIT HCV P7 ION CHANNEL ACTIVITY

CROSS-REFERENCE TO RELATED APPLICATIONS

This application is a continuation-in-part of U.S. application Ser. No. 10/031,145, filed on Jul. 3, 2002, which is the National Stage of International Application No. PCT/US00/21732, filed Aug. 10, 2000, which claims the benefit under 35 U.S.C. § 119(e) of U.S. Application Ser. No. 60/198,621, filed on Apr. 20, 2000 and U.S. Application Ser. No. 60/148,101, filed on Aug. 10, 1999. This application claims the benefit under 35 U.S.C. § 119(e) of U.S. Application Ser. No. 60/412,560, filed on Sep. 23, 2002. U.S. application Ser. No. 10/031,145 and U.S. Application Ser. No. 60/412,560 are incorporated herein by reference in their entireties.

BACKGROUND

Hepatitis C virus (HCV) is the major cause of chronic hepatitis with a significant risk of end-stage liver cirrhosis and hepatocellular carcinoma. (See Di Bisceglie, A. M., (1997) *Hepatology* 26(3 Suppl. 1): 345-385). HCV belongs to the family Flaviviridae, which consists of three genera: flaviviruses, pestiviruses, and hepaciviruses. In the absence of both a suitable small animal model and a reliable in vitro infectivity assay for HCV, potential antiviral drugs are initially tested using a related pestivirus, bovine viral diarrhea virus (BVDV). BVDV in vitro infectivity assays have been used to demonstrate that alkylated iminosugar derivatives containing either the glucose analogue 1,5-Dideoxy-1,5-imino-D-glucitol, also called deoxynojirimycin or "DNJ," or the galactose analogue 1,5-Dideoxy-1,5-imino-D-galactitol, also called deoxygalactonojirimycin or "DGJ," are potent antiviral inhibitors. (See Durantel, D., et al., (2001) *J. Virol.* 75(19): 8987-98).

DNJ derivatives are antiviral inhibitors at least partially because they inhibit ER α-glucosidases I and II. These enzymes remove three glucose residues that form part of N-glycan precursors, which are transferred en bloc to nascent glycoproteins in the ER. ER α-glucosidase inhibition prevents the formation and subsequent interaction of monoglucosylated, N-linked oligosaccharide-containing glycoproteins with the ER resident chaperones calnexin and calreticulin. (See Bergeron, J. J., et al., (1994) *Trends Biochem. Sci.* 19(3): p. 124-8; Peterson, J R., et al., (1995) *Mol. Biol. Cell* 6(9): 1173-84). Calnexin interaction is crucial for the proper folding of many host and virus encoded glycoproteins, including the envelope glycoproteins of BVDV and HCV. (See Branza-Nichita, N., et al., (2001) *J Virol.* 75(8): 3527-36; Choukhi, A., et al., (1998) *J. Virol.*, 1998 72(5): 3851-8). Misfolding of BVDV envelope glycoproteins may lead to an impaired secretion of virions from infected cells.

Previous experiments have shown that the antiviral effect of the long alkylchain derivative N-nonyl-DNJ (NN-DNJ) is more pronounced than that of the short alkylchain derivative N-butyl-DNJ (NB-DNJ), although the latter achieves a more effective ER α-glucosidase inhibition in cellulo. (See Durantel, D., et al., (2001) *J. Virol.* 75(19): 8987-98). In addition, long alkylchain DGJ-derivatives which are not recognized by and do not inhibit ER α-glucosidases, also show potent antiviral activity. Therefore, ER α-glucosidase inhibition does not directly correlate with the observed antiviral effect and is ruled out as the sole antiviral mechanism.

The additional mechanism of action is apparently associated with the length of the alkyl sidechain, as the short-chain N-butyl-DGJ (NB-DGJ) shows no antiviral activity, whereas the long alkylchain derivative NN-DGJ is a potent inhibitor. It is, however, not associated with a detergent-like effect of the amphiphilic, alkylated iminosugar derivatives, as the structurally similar detergents n-octyl glucoside (n-OG) and n-nonyl glucoside are not antiviral in in vitro BVDV infectivity assays. (See Durantel, D., et al., (2001) *J. Virol* 75(19): 8987-98). Drug treatment affects the dimerization of viral membrane glycoproteins and alters the membrane glycoprotein composition of secreted BVDV virions, but does not influence either viral RNA replication or protein synthesis.

Because of their ER α-glucosidase inhibitory activity, both long and short alkylchain DNJ-derivatives are antiviral against flaviviruses like Dengue virus (DENV) and Japanese Encephalitis virus (JEV). (See Courageot, M. P., et al., (2000) *J Virol.* 74(1): 564-72; Wu, S. F., et al., (2002) *J. Virol.*, 76(8): 3596-604). In contrast, DGJ-derivatives show no antiviral activity against flaviviruses, but the long alkylchain DGJ-derivatives are potent inhibitors of pestiviruses. Unlike the closer related pesti- and hepaciviruses, flaviviruses do not contain p7 or an equivalent small membrane spanning protein. As such, DNJ- and DGJ-derivatives may inhibit viral replication by inhibiting p7 or equivalent proteins.

The HCV positive stranded RNA genome encodes a single polyprotein precursor of approximately 3000 amino acid residues. The polyprotein is co- and post-translationally processed by viral and cellular proteases to produce the mature structural and non-structural proteins C, El, E2, p7, NS2, NS3, NS4A, NS4B, NS5A and NS5B (reviewed in Reed, K. E. and C. M. Rice, (2000) *Curr. Top. Microbiol. Immunol.* 242: p. 55-84.), with a potential further F protein arising from a ribosomal frameshift in the N-terminal region of the polyprotein. (See Xu, Z., et al., (2001) *EMBO J.* 20(14): p. 3840-8). Although most cleavages in the polyprotein precursor are efficiently completed during or immediately after translation, cleavages are delayed at the E2/p7 and p7/NS2 sites, leading to the production of an E2-p7-NS2 precursor. Furthermore, processing between E2 and p7 is incomplete resulting in the production of E2-p7 as well as E2 and p7. (See Lin, C., et al., (1994) *J. Virol.* 68(8): p. 5063-73; Mizushima, H., et al., (1994) *J. Virol.* 68(10): p. 6215-22).

Because a cell culture model for HCV replication is unavailable, information about HCV replication is derived by using a BVDV cell culture model. As such, most functional data about p7 are derived from studying BVDV p7, a 70 amino acid protein very similar to HCV p7. Functional data about BVDV p7 has been obtained by introducing mutations into an infectious cDNA clone of BVDV. An in-frame deletion of the entire p7 gene does not affect BVDV RNA replication, but does lead to the production of non-infectious virions. However, infectious viral particles can be generated by complementing p7 in trans. (See Harada, T., N. Tautz, and H. J. Thiel, (2000) *J. Virol.* 74(20): 9498-506), which suggests that the pestivirus p7 is essential for the production of infectious progeny virus.

The HCV p7 protein is a 63 amino acid peptide which has been shown to be a polytopic membrane protein that crosses the membrane twice and has its N- and C-termini oriented towards the extracellular environment. (See Carrere-Kremer, S., et al., (2002) *J. Virol.* 76(8): 3720-30). As such, the p7 protein has been shown to include two transmembrane domains. The N-terminal transmembrane domain includes amino acids from about position 10 to about position 32 and the C-terminal transmembrane domain includes amino acids form about position 36 to about position 58. Although the amino acids within the two transmembrane domains are somewhat variable among all HCV strains, for reported strains, a majority of amino acids within the transmembrane domains, (typically greater than about 70%), are members of a hydrophobic group characterized as F, I, W, Y, L, V, M, P, C, and A. The two transmembrane domains are linked by three non-hydrophobic amino acids, (K or R, G, R or K), and a consensus sequence for p7 is ALENLVVLNAASAAGHT-GILWFLVFFCAAWYVKGLRVPGATYSLLGLWPLLL LLLALPQRAYA (SEQ ID NO.: 1). (See Carrere-Kremer, S., et al., (2002) *J. Virol.* 76(8): 3720-30).

Subgenomic replicon studies have shown that the p7 of HCV is not necessary for genome replication. (See Lohmann, V., et al., (1999) *Science* 285(5424): p. 110-3; Pietschmann, T., et al., (2001) *J. Virol.* 75(3): p. 1252-64), but its role in infectious virus production is unknown. HCV p7 has been suggested to be a putative member of a group of small proteins known as viroporins, which mediate cation permeability across membranes and are important for virion release or maturation. For some viroporins, the transmembrane domain has been shown to be sufficient to form membrane channels. (See Duff, K. C. and R. H. Ashley, (1992) *Virology* 190(1): p. 485-9; Fischer, W. B., et al., (2001) *Eur. Biophys. J.* 30(6): p. 416-20).

SUMMARY

One embodiment relates to a method of treating HCV infection by administering iminosugar derivative compounds effective to inhibit the activity of HCV p7 protein in a subject in need thereof, particular a human. The compounds employed in the described method are effective at inhibiting the capability of HCV p7 protein to permeabilize membranes. In the broadest aspect, the compounds are represented by the following Formula I or II:

I

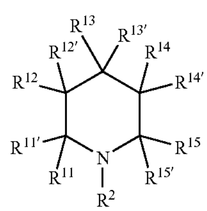

II 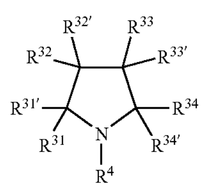 wherein each of $R^{11}$, $R^{11'}$, $R^{12}$, $R^{12'}$, $R^{13}$, $R^{13'}$, $R^{14}$, $R^{14'}$, $R^{15}$, $R^{15'}$, $R^{31}$, $R^{31'}$, $R^{32}$, $R^{32'}$, $R^{33}$, $R^{33'}$, $R^{34}$, and $R^{34'}$ is selected, independently from each other, from the group consisting of —H; —OH; —F; —Cl; —Br; —I; —$NH_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; -(alkylene) oxy(alkyl); —CN; —$NO_2$; —COOH; —COO(alkyl); —COO(aryl); —C(O)NH($C_{1-6}$ alkyl); —C(O)NH (aryl); sulfonyl; ($C_{1-6}$ alkyl)sulfonyl; arylsulfonyl; sulfamoyl, ($C_{1-6}$ alkyl)sulfamoyl; ($C_{1-6}$ alkyl)thio; ($C_{1-6}$ alkyl)sulfonamide; arylsulfonamide; —$NHNH_2$; —NHOH; aryl; and heteroaryl, wherein each of the substituents may be the same or different.

$R^2$ and $R^4$ are substituents selected independently of each other from the group consisting of linear $C_{7-18}$ alkyl, substituted $C_{1-18}$ alkyl, branched $C_{3-18}$ alkyl, $C_{2-18}$ alkenyl and alkynyl, and aralkyl. Each linear $C_{7-18}$ alkyl, branched $C_{3-18}$ alkyl, $C_{2-18}$ alkenyl and alkynyl, and aralkyl optionally may be substituted, and the substituted $C_{1-18}$ alkyl is substituted with one or more substituents independently selected from the group consisting of —OH; —F; —Cl; —Br; —I; —$NH_2$; alkyl- and dialkylamino; linear or branched $C_{1-6}$ alkyl, $C_{2-6}$ alkenyl and alkynyl; aralkyl; linear or branched $C_{1-6}$ alkoxy, aryloxy; aralkoxy; —CN; —$NO_2$; —COOH; —COO(alkyl); —COO(aryl); —C(O)NH($C_{1-6}$ alkyl); —C(O)NH(aryl); sulfonyl; ($C_{1-6}$ alkyl)sulfonyl; arylsulfonyl; sulfamoyl, ($C_{1-6}$ alkyl)sulfamoyl; ($C_{1-6}$ alkyl)thio; ($C_{1-6}$ alkyl)sulfonamide; arylsulfonamide; —$NHNH_2$; and —NHOH, wherein selected substituents may be the same or different. Particularly suitable substituents include nonyl, 7-oxanonyl, and 10-oxaundecyl, and particularly desirable compounds include N-nonyldeoxynojirimycin (NN-DNJ), N-nonyldeoxygalactonojirimycin (NN-DGJ), N-7-oxanonyl-6-methyldeoxygalactonojirimycin (i.e., N-7-oxanonyl-6-deoxy-DGJ, N-7-oxanonyl-1,6,-dideoxygalactonojirimycin, or N-7-oxanonyl-methyl-DGJ), and N-10-oxaundecyl-1,6-dideoxygalactonojirimycin (i.e., N-10-oxaundecyl-6-methyldeoxyglactonojirimycin, N-10-oxaundecyl-methyl-DGJ, N-10-oxaundecyl-6-deoxy-DGJ, (2R, 3S, 4R, 5S)-1-(9-methoxynonyl)-2-methyl-3,4,5-piperidinetriol, (2R, 3R)-2,3-dihydroxybutanedioate (1:1), or SP240).

One or more of the compounds may be packaged as a kit for treating HCV infection. The kit may include instructions for treating HCV infection as well as implements for administering the compounds.

Another embodiment relates to a method of screening compounds for the capability to inhibit HCV p7 activity. In particular, compounds may be screened based on whether the compound inhibits the capability of p7 or a variant of p7 to permeabilize membranes. In such a method, it may be desirable to utilize an artificial membrane system or a bacterial system.

BRIEF DESCRIPTION OF THE DRAWINGS

FIG. 1A shows the growth curves of *E. coli* Rosetta gami(DE3)pLacl cells. The optical densities ($OD_{600\ nm}$) of non-transformed cells (A), cells transformed with pTriEx1.1 (B), and pTiEx1.1p7 (C) were monitored at the indicated times (hours post induction). Growth curves of uninduced cells (open circles) and cells induced by addition of 1 mM IPTG (open squares) are shown. FIG. 1B shows the release of [$^3$H]-uridine by non-transformed *E. coli* Rosetta gami (DE3)pLacl cells (A), cells transformed with pTriEx1.1 (B), and pliEx1.1p7 (C) at the indicated times. Growth curves of un-induced cells (open circles) and cells induced by addition of 1 mM IPTG (open squares) are shown.

FIG. 2 shows a Tris-tricine gel electrophoresis analysis of synthetic HCV p7. The gel was silver-stained (left panel) or transferred to a membrane which was subsequently probed with streptavidin (right panel).

FIG. 3A shows channel recordings of synthetic HCV p7 reconstituted into a BLM. Straight lines denote the closed state. FIG. 3B shows a current trace recorded after approximately 30 minutes of data collection. FIG. 3C shows a current histogram of the trace recorded at +100 mV membrane potential as shown in FIG. 3A.

Figure 6:
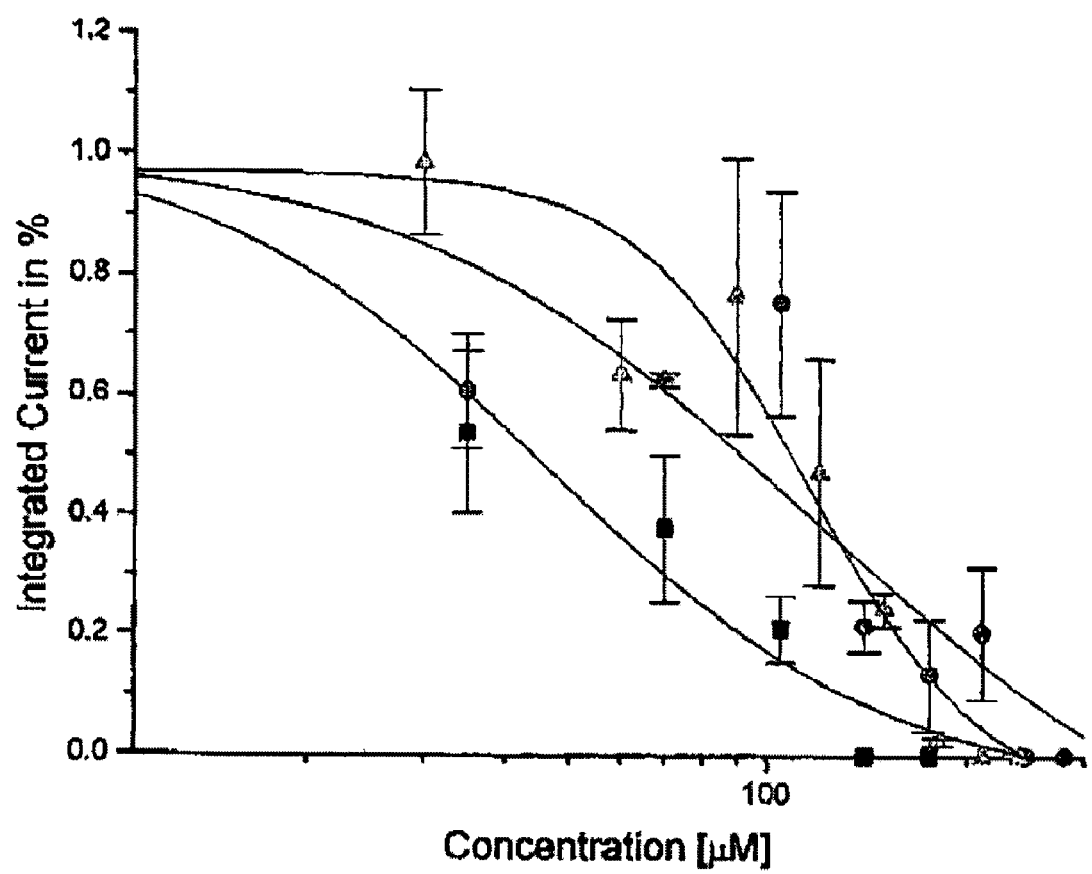

FIG. 6 shows a graphical representation of the normalized, integrated current traces and standard deviation versus drug concentration. The data represent the average of three representative trace slices of 4 seconds for NN-DNJ (squares) and NN-DGJ (diamonds), and three representative trace slices of 30 seconds for N7-oxanonyl-6-deoxy-DGJ (triangles). The approximate binding constants ($K_{app}$), as deduced by a sigmoidal fit of the data according to the formula "integrated current"=$1/(1+([drug]/K_{app}))$, are: for NN-DNJ, $K_{app}$=45.2 (±10.7) μM; for NN-DGJ, $K_{app}$=110.4 (±19.9) μM; and for N7-oxanonyl-6-deoxy-DGJ, $K_{app}$=114.2 (±18.3) μM.

Figure 7:
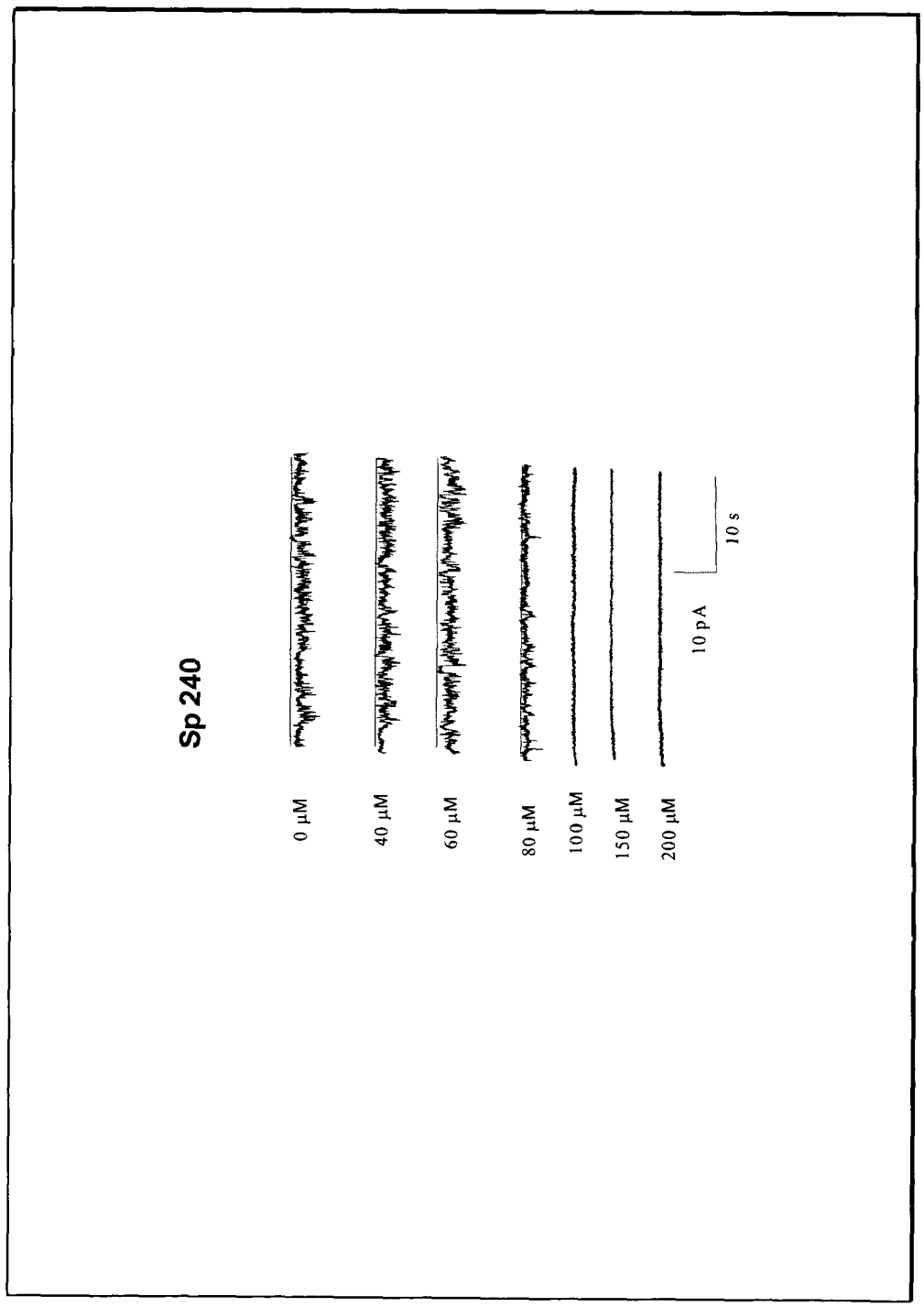

FIG. 7 shows the effect of SP240 (i.e., N-10-oxaundecyl-1,6-dideoxygalactonojirimycin) on p7 channel signals in BLM.

DEFINITIONS

Unless otherwise specified, the terms "a" or "an" mean "one or more."

Unless otherwise specified, the term "alkyl" as used herein refers to straight- and branched-chain alkyl radicals containing one or more carbon atoms and includes, for example, methyl, ethyl, butyl, and nonyl.

The term "aryl" as used herein refers to a monocyclic aromatic group such as phenyl or a benzo-fused aromatic group such as indanyl, naphthyl, or fluorenyl and the like.

The term "heteroaryl" refers to aromatic compounds containing one or more hetero atoms. Examples include pyridyl, furyl, and thienyl or a benzofused aromatic containing one or more heteroatoms such as indolyl or quinolinyl.

The term "heteroatom" as used herein refers to non-carbon atoms such as N, O, and S.

The term "cycloalkyl" as used herein refers to a carbocyclic ring containing 3, 4, 5, 6, 7, or 8 carbons and includes, for example, cyclopropyl and cyclohexyl.

Unless otherwise specified, the term "alkoxy" as used herein refers to a straight- or branched-chain alkoxy containing one or more carbon atoms and includes, for example, methoxy and ethoxy.

The term "alkenyl" as used herein refers to a straight or branched-chain alkyl containing one or more double bonds such as ethenyl and propenyl.

The term "aralkyl" as used herein refers to an alkyl substituted with an aryl such as benzyl and phenethyl.

The term "alkynyl" as used herein refers to a straight or branched-chain alkyl containing one or more triple bonds such as ethynyl and propynyl.

The term "aryloxy" as used herein refers to a substituent created by replacing the hydrogen atom in an —OH group with an aryl group, and includes, for example, phenoxy.

The term "aralkoxy" as used herein refers to an alkoxy group substituted with an aryl group, such as 2-phenylethoxy.

The term "alkylamino" as used herein refers to an amino group substituted with one alkyl group such as methylamino (—NHCH$_3$) and ethylamino (—NHCH$_2$CH$_3$).

The term "dialkylamino" as used herein refers to an amino group substituted with two alkyl groups such as dimethylamino (—N(CH$_3$)$_2$) and diethylamino (—N(CH$_2$CH$_3$)$_2$).

The term "DNG" as used herein means 1,5-Dideoxy-1,5-imino-D-glucitol or "deoxynojirimycin."

The term "DGJ" as used herein means 1,5-Dideoxy-1,5-imino-D-galactitol or "deoxygalactonojirimycin."

The term "BLM" as used herein means "black lipid membranes."

DETAILED DESCRIPTION OF THE PREFERRED EMBODIMENTS

The compounds employed in the disclosed method are effective as inhibitors of HCV p7. In the broadest aspect, the compounds are represented by Formula I or II:

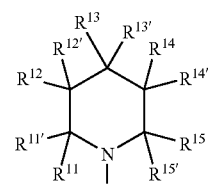

I

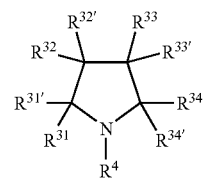

II

In one aspect, the method contemplates administering compounds of Formula I. Each of $R^{11}$, $R^{11'}$, $R^{12}$, $R^{12'}$, $R^{13}$, $R^{13'}$, $R^{14}$, $R^{14'}$, $R^{15}$, and $R^{15'}$ is selected, independently from the other, from the group consisting of —H; —OH; —F; —Cl; —Br; —I; —NH$_2$; alkyl- and dialkylamino; linear or branched C$_{1-6}$ alkyl, C$_{2-6}$ alkenyl and alkynyl; aralkyl; linear or branched C$_{1-6}$ alkoxy; aryloxy; aralkoxy; -(alkylene)oxy(alkyl); —CN; —NO$_2$; —COOH; —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-6}$ alkyl)thio; (C$_{1-6}$ alkyl)sulfonamide; arylsulfonamide; —NHNH$_2$; —NHOH; aryl; and heteroaryl. Each substituent may be the same or different.

In a preferred embodiment, at least one of $R^{11}$, $R^{11'}$, $R^{12}$, $R^{12'}$, $R^{13}$, $R^{13'}$, $R^{14}$, $R^{14'}$, $R^{15}$, and $R^{15'}$ is a hydroxymethyl group (—CH$_2$OH). Alternatively, at least one of $R^{11}$, $R^{11'}$, $R^{12}$, $R^{12'}$, $R^{13}$, $R^{13'}$, $R^{14}$, $R^{14'}$, $R^{15}$, and $R^{15'}$ is a hydroxy group (—OH). The most preferred embodiment contemplates at least two of $R^{11}$, $R^{11'}$, $R^{12}$, $R^{12'}$, $R^{13}$, $R^{13'}$, $R^{14}$, $R^{14'}$, $R^{15}$, and $R^{15'}$ being selected from —CH$_3$, —CH$_2$OH, and —OH.

$R^2$ is a substituent selected from linear C$_{7-18}$ alkyl, substituted C$_{1-18}$ alkyl, branched C$_{3-18}$ alkyl, C$_{2-18}$ alkenyl and alkynyl, and aralkyl. Each linear C$_{7-18}$ alkyl, branched C$_{3-18}$ alkyl, C$_{2-18}$ alkenyl and alkynyl, and aralkyl optionally may be substituted, and the substituted C$_{1-18}$ alkyl is substituted with one or more groups independently selected from —OH; —F; —Cl; —Br; —I; —NH$_2$; alkyl- and dialkylamino; linear or branched C$_{1-6}$ alkyl, C$_{2-6}$ alkenyl and alkynyl; aralkyl; linear or branched C$_{1-6}$ alkoxy, aryloxy; aralkoxy; —CN; —NO$_2$; —COOH; —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-18}$ alkyl)thio; (C$_{1-6}$ alkyl)sulfonamide; arylsulfonamide; —NHNH$_2$; and —NHOH.

Preferably, $R^2$ is a linear $C_{7-18}$ alkyl, branched $C_{3-18}$ alkyl, or substituted $C_{1-18}$ alkyl group. More preferably, $R^2$ is a linear $C_{7-11}$ alkyl, branched $C_{7-11}$ alkyl, substituted $C_{7-11}$ alkyl, or linear or branched $C_{1-18}$ alkyl substituted with a $C_{1-6}$ alkoxy. Examples of $R^2$ that are linear $C_{7-11}$ alkyl substituents include heptyl, octyl, and nonyl. An example of $R^2$ being a substituted alkyl group is 7-oxanonyl (—$CH_2$(CH$_2$)$_5$—O—$CH_2CH_3$). Most preferably, $R^2$ is n-nonyl, 7-oxanonyl, or 10-oxaundecyl.

In certain embodiments of Formula I, the compound may be represented as one of the following formulas:

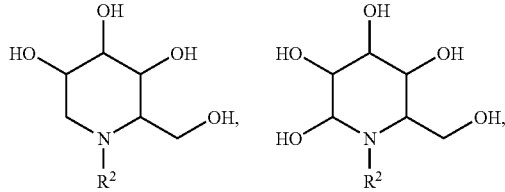

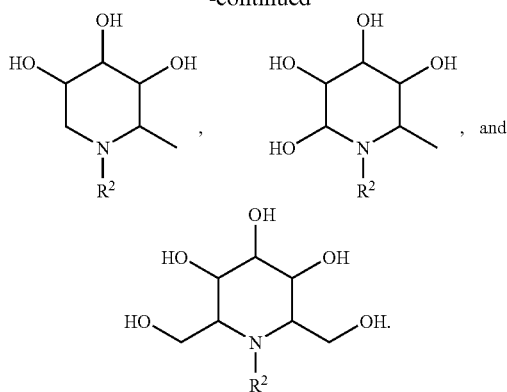

The stereochemistry at each ring carbon atom in the formulas above may vary independently from that in the other ring carbon atoms. More preferably, the compound has one of the formulas as set forth in Table 1:

TABLE I

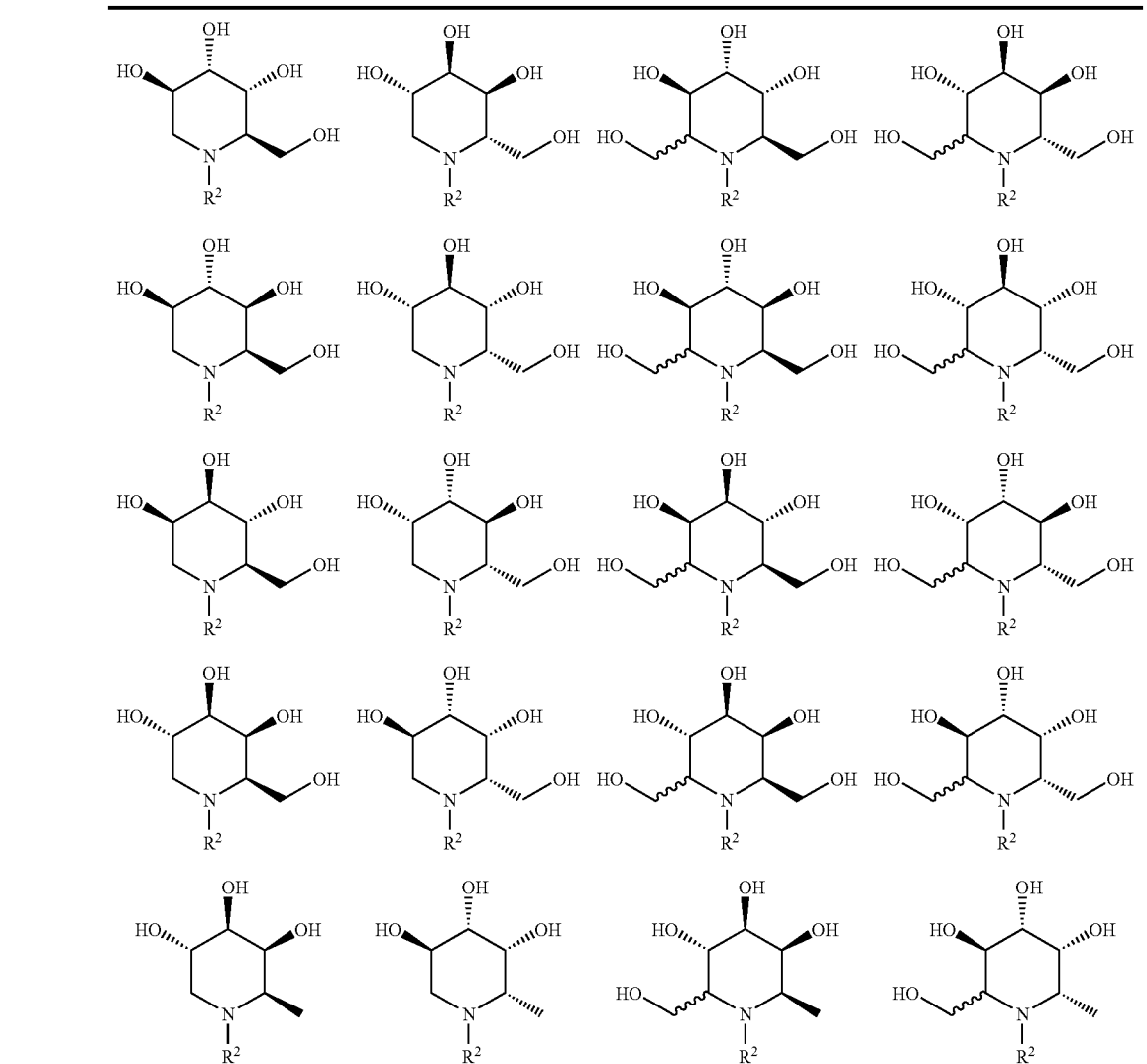

TABLE I-continued

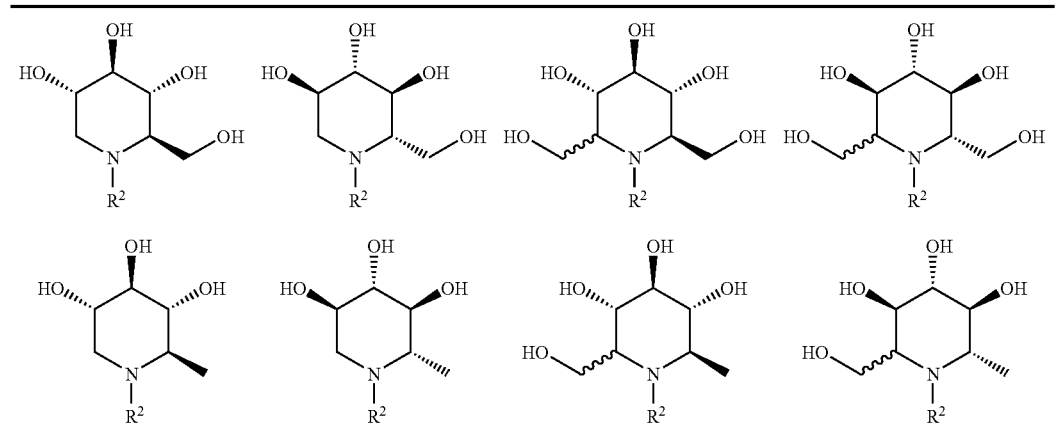

More preferably, the compound has one of the formulas:

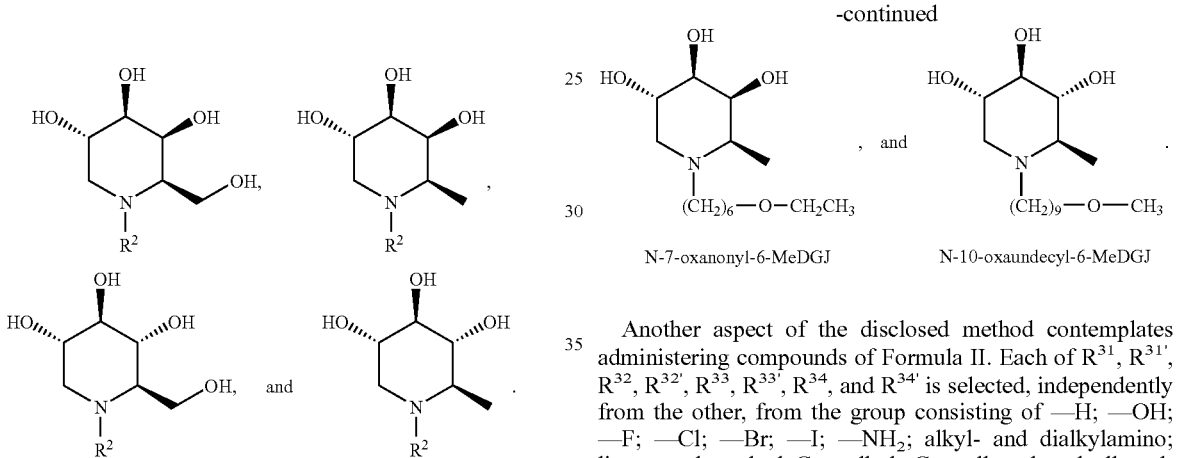

N-7-oxanonyl-6-MeDGJ    N-10-oxaundecyl-6-MeDGJ

Still more preferably, $R^2$ is nonyl, 7-oxanonyl, or 10-oxaundecyl, and the most preferred compounds include N-nonyldeoxynojirimycin (NN-DNJ), N-nonyldeoxygalactonojirimycin (NN-DGJ), N-7-oxanonyl-6-methyldeoxygalactonojirimycin (i.e., N-7-oxanonyl-6-deoxy-DGJ, N-7-oxanonyl-1,6,-dideoxygalactonojirimycin, or N-7-oxanonyl-methyl-DGJ), and N-10-oxaundecyl-1,6-dideoxygalactonojirimycin (i.e., N-10-oxaundecyl-6-methyldeoxyglactonojirimycin, N-10-oxaundecyl-methyl-DGJ, N-10-oxaundecyl-6-deoxy-DGJ, (2R, 3S, 4R, 5S)-1-(9-methoxynonyl)-2-methyl-3,4,5-piperidinetriol, (2R, 3R)-2,3-dihydroxybutanedioate (1:1), or SP240) and their isomers, for example:

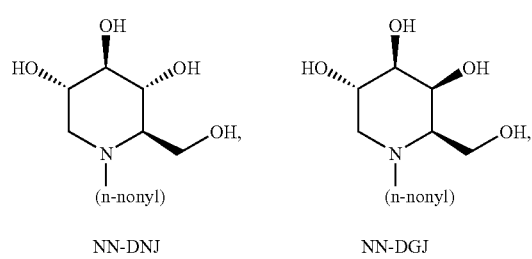

NN-DNJ    NN-DGJ

Another aspect of the disclosed method contemplates administering compounds of Formula II. Each of $R^{31}$, $R^{31'}$, $R^{32}$, $R^{32'}$, $R^{33}$, $R^{33'}$, $R^{34}$, and $R^{34'}$ is selected, independently from the other, from the group consisting of —H; —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; -(alkylene)oxy(alkyl); —CN; —NO$_2$; —COOH; —COO (alkyl); —COO(aryl); —C(O)NH($C_{1-6}$ alkyl); —C(O)NH (aryl); sulfonyl; ($C_{1-6}$ alkyl)sulfonyl; arylsulfonyl; sulfamoyl; ($C_{1-6}$ alkyl)sulfamoyl; ($C_{1-6}$ alkyl)thio; ($C_{1-6}$ alkyl)sulfonamide; arylsulfonamide; —NHNH$_2$; —NHOH; aryl; and heteroaryl. Each substituent may be the same or different.

In a preferred embodiment, at least one of $R^{31}$, $R^{31'}$, $R^{32}$, $R^{32'}$, $R^{33}$, $R^{33'}$, $R^{34}$, and $R^{34'}$ is a hydroxymethyl group (—CH$_2$OH). Alternatively, at least one of $R^{11}$, $R^{11'}$, $R^{12}$, $R^{12'}$, $R^{13}$, $R^{13'}$, $R^{14}$, $R^{14'}$, $R^{15}$, and $R^{15'}$, is a hydroxy group (—OH). The most preferred embodiment contemplates at least two of $R^{11}$, $R^{11'}$, $R^{12}$, $R^{12'}$, $R^{13}$, $R^{13'}$, $R^{14}$, $R^{14'}$, $R^{15}$, and $R^{15'}$, being selected from —CH$_3$, —CH$_2$OH, and —OH.

In Formula II, $R^4$ is a substituent selected from linear $C_{7-18}$ alkyl, substituted $C_{1-18}$ alkyl, branched $C_{3-18}$ alkyl, $C_{2-18}$ alkenyl and alkynyl, and aralkyl. Each linear $C_{7-18}$ alkyl, branched $C_{3-18}$ alkyl, $C_{2-18}$ alkenyl and alkynyl, and aralkyl optionally may be substituted, and each substituted $C_{1-18}$ alkyl is substituted with one or more groups independently selected from —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; —CN; —NO$_2$; —COOH; —COO (alkyl); —COO(aryl); —C(O)NH($C_{1-6}$ alkyl); —C(O)NH (aryl); sulfonyl; ($C_{1-6}$ alkyl)sulfonyl; arylsulfonyl; sulfamoyl, ($C_{1-6}$ alkyl)sulfamoyl; ($C_{1-6}$ alkyl)thio; ($C_{1-6}$ alkyl) sulfonamide; arylsulfonamide; —NHNH$_2$; and —NHOH.

Preferably, $R^4$ is a linear $C_{7-18}$ alkyl, branched $C_{3-18}$ alkyl, or substituted $C_{1-18}$ alkyl group. More preferably, $R^4$ is a linear $C_{7-11}$ alkyl, branched $C_{7-11}$, alkyl, substituted $C_{7-11}$ alkyl, or linear or branched $C_{1-18}$ alkyl substituted with a $C_{1-6}$ alkoxy. Examples of $R^4$ that are linear $C_{7-11}$ alkyl substituents include heptyl, octyl, and nonyl. An example of $R^4$ being a substituted alkyl group is 7-oxanonyl (—CH$_2$(CH$_2$)$_5$—O—CH$_2$CH$_3$). Most preferably, $R^4$ is n-nonyl, 7-oxanonyl, or 10-undecyl.

In one embodiment, disclosed is a method for treating an HCV infection that includes contacting either the HCV p7 protein or components of a membrane that includes the p7 protein with one or more compounds that inhibit the activity of the p7 protein. The inventors have shown that the p7 protein increases the permeability of membranes, likely by functioning as a membrane channel protein. In addition, the inventors have shown that particular compounds can inhibit the ability of p7 to permeabilize membranes. However, the disclosed method contemplates that the compounds disclosed herein may inhibit other activities of p7 protein as well.

The selected compound may inhibit one or more activities of the p7 protein by interacting with the protein. In this instance, it may be desirable to select a compound that binds the p7 protein with an apparent binding constant of no more than about $K_{app}$=130 µM (i.e., $K_{app}$=114.2 (±18.3) µM), as shown in particular binding assays. Alternatively, it may be desirable to select a compound that blocks the ability of p7 protein to permeabilize membranes when the compound is present at a concentration of no more than about 180 µM, as shown in particular permeability assays.

Where the selected compound inhibits the capability of p7 to permeabilize membranes, the compound may prevent p7 from forming channels, or the compound may block the channel after it has formed, (i.e., as a channel blocker). Alternatively, the compound may inhibit the p7 protein by interacting with one or more components of the membrane, such as phospholipids, thereby changing the membrane's fluidity or local characteristics. As such, the compound may inhibit the capability of p7 to form functional membrane channels.

In yet another embodiment, a method is provided for screening for a potential antiviral agent effective to inhibit activity of HCV p7. Typically, the method comprises incorporating p7 or a variant of p7 into a membrane system and observing an increase in permeability, e.g., by recording electrical currents through the membrane using standard methods. Test compounds are then added to the membrane system to determine whether the compound inhibits the ability of p7 to permeabilize membranes. Ideal compounds may completely block the ability of p7 to permeabilize membranes at concentrations of no more than about 180 µM.

Black lipid membranes ("BLM") may be used in the method, but other membrane systems may be utilized as well. Black lipid membranes are well known in the art, and BLM are commonly used to study membrane permeability, e.g., as mediated by channel-forming proteins. (See Duff, K. C. and R. H. Ashley, (1992) *Virology* 190(1): p. 485-9).

After a suitable membrane system for observing p7 activity has been selected, p7 may be incorporated into the membranes to form p7-containing membranes. The p7 protein may be selected from any HCV strain where the p7 protein can be shown to increase the permeability of a selected membrane. For example, the p7 protein from the HCV-H strain may be selected (i.e., ALENLVIL-NAASLAGTHLGVSFLVFFCFAW-YLKGRVWPGAVYALYGMWPLLL LLLALPQRAYA (SEQ ID NO.: 1)), or the p7 protein from another strain may be selected. It may be desirable to use a p7 consensus sequence, obtained by comparing the amino acid sequences of reported p7 proteins, or it may be desirable to select a p7 protein from a particular HCV lade, (e.g., clade 1).

In another embodiment of the screening method, it may be desirable to use a variant of the selected p7 protein, provided that the variant is functional (e.g., the variant may be shown to permeabilize a chosen membrane as determined by methods known in the art). Possible variants include fusions, deletions, and/or mutations or substitutions. For example, it may be desirable to create a biotinylated p7 protein for use in the described method. In another example, it may be desirable to use at least those portions of p7 or a derivative of p7 that can be shown to permeabilize a chosen membrane (e.g., a selected p7 protein or variant may demonstrate a conductance level in a BLM of no less than about 60 pS (i.e., 86±22 pS)). It also may be desirable to create mutations within a selected p7 amino acid sequence. Where mutations are created, it may be desirable to maintain the defining characteristic of the amino acid at a given position based on comparisons between HCV strains. For example, a comparison of the p7 sequences from different HCV strains has shown that certain amino acid positions may be characterized as "hydrophobic," "neutral," or "hydrophilic." (See Carrere-Kremer, S., et al., (2002) *J. Virol.* 76(8): 3720-30). A "hydrophobic amino acid" may be characterized as belonging to the group F, I, W, Y, L, V, M, P, C, and A.

The chosen p7 protein or variant may be synthesized artificially or expressed in a suitable biological system, such as bacterial or eukaryotic cells. After the protein has been incorporated into the selected membrane system, the permeability of the membranes may be measured to determine whether the protein demonstrates activity (e.g., causing an increase in permeability or a decrease in cell viability). Test compounds may be contacted with the protein and/or components of the p7-containing membranes to determine whether the compounds inhibit the activity of the protein. In the described method, the test compounds may be contacted with p7 and/or the components of the p7-containing membranes before and/or after p7 has been incorporated into the membranes.

In one embodiment, it may be desirable to use iminosugar derivatives as test compounds in the screening method. In particular, it may be desirable to use alkylated derivatives of DGJ or DNJ as described herein as test compounds. Derivatives of the alkylated imino sugars N-nonyldeoxynojirimycin (NN-DNJ), N-nonyldeoxygalactonojirimycin (NN-DGJ), N-7-oxanonyl-6-methyldeoxygalactonojirimycin (i.e., N-7-oxanonyl-6-deoxy-DGJ, N-7-oxanonyl-1,6,-dideoxygalactonojirimycin, or N-7-oxanonyl-methyl-DGJ), and N-10-oxaundecyl-1,6-dideoxygalactonojirimycin (i.e., N-10-oxaundecyl-6-methyldeoxyglactonojirimycin, N-10-oxaundecyl-methyl-DGJ, N-10-oxaundecyl-6-deoxy-DGJ, (2R, 3S, 4R, 5S)-1-(9-methoxynonyl)-2-methyl-3,4,5-piperidinetriol, (2R, 3R)-2,3-dihydroxybutanedioate (1:1), or SP240) and/or their isomers may be particularly desirable.

In another embodiment, it may be desirable to use compounds or derivatives thereof that have been shown to interact with p7 or other membrane components as test compounds in the method (e.g., compounds that have been shown to interact with p7 in vitro). In yet another embodiment, it may be desirable to use compounds that have been shown to disrupt channel formation either by p7 or other proteins, and/or compounds that are known blockers of channels formed by p7 or other proteins, or derivatives thereof, as test compounds in the method. For example, amantadine is a known channel blocker of influenza A virus M2 channels. (See Hay, A. J., et al., (1985) *EMBO J.* 4(11): p. 3021-4; Duff, K. C. and R. H. Ashley, (1992) *Virology* 190(1): p. 485-9; Sunstrom, N. A., et al., (1996) *J. Membr. Biol.* 150(2): p. 127-32; Fischer, W. B., et al., (2001) *Eur. Biophys. J.* 30(6): p. 416-20). Recently, others have suggested that p7 forms an ion channel that is blocked by amantadine. (See Griffin et al., *FEBS Letters,* 2003, Jan. 20; 535(1-3):34-8). As such, it may be desirable to use amantadine or derivatives thereof as test compounds in the method.

In one embodiment, an inducible bacterial system may be utilized to observe permeability, where an increase in the permeability of the bacterial cell membranes may lead to an arrest in cell growth. For example, p7 or a variant thereof may be expressed from an inducible promoter in a suitable bacteria system to determine if the cells display an arrest in cell growth. Alternatively, an increase in permeability can be verified by labeling the cells with a radioactive molecule such as [$^3$H]-uridine prior to induction of p7 expression. After induction of p7 expression, permeability can be assessed by measuring the release of [$^3$H]-uridine into the media. Test compounds may be administered to the bacteria to determine whether the compounds prevent cell growth arrest and/or whether the compounds prevent release of [$^3$H]-uridine into the media.

Preparation of the Compounds

Compounds for use in the methods described herein may be prepared from commercially available imino compounds used as starting materials. Commercial sources include Sigma, St. Louis, Mo.; Cambridge Research Biochemicals, Norwich, Cheshire, United Kingdom; and Toronto Research Chemicals, Ontario, Canada.

Alternatively, the present compounds can be prepared by synthetic methods known to those skilled in the art. For example, the syntheses of a variety of deoxynojirimycin (DNJ) derivatives are described in U.S. Pat. Nos. 5,622,972; 5,200,523; 5,043,273; 4,944,572; 4,246,345; 4,266,025; 4,405,714; and 4,806,650 and in U.S. application Ser. No. 10/031,145. Other imino sugar compounds described herein are known and may be prepared by methods set forth in U.S. Pat. Nos. 4,861,892; 4,894,388; 4,910,310; 4,996,329; 5,011,929; 5,013,842; 5,017,704; 5,580,884; 5,286,877; 5,100,797; and 6,291,657.

Pharmaceutical Compositions

Where it is desirable to administer the compounds as a pharmaceutical composition or medicament, the compounds disclosed herein can be formulated for a variety of modes of administration. Techniques and formulations generally may be found in REMINGTON'S PHARMACEUTICAL SCIENCES (18th ed.), Mack Publishing Co. (1990).

The medicaments may be adapted for administration by any appropriate route, for example by the oral (including buccal or sublingual), rectal, nasal, topical (including buccal, sublingual or transdermal), or parenteral (including subcutaneous, intramuscular, intravenous or intradermal) route although oral administration is preferred. Such a composition may be prepared by any method known in the art of pharmacy, for example by admixing the active ingredient with a carrier under sterile conditions.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/disphosphate, polygalacturonate, salicylate, stearate, subacetate, succinate, sulfate, tannate, tartrate, or teoclate. Other pharmaceutically acceptable salts may be found, for example, in REMINGTON'S PHARMACEUTICAL SCIENCES (18th ed.), supra.

Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

For injection, the compounds and agents may be formulated in aqueous solutions, preferably in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the methods into dosages suitable for systemic administration is within the scope of the methods. With proper choice of carrier and suitable manufacturing practice, the compositions of the present methods, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the methods to be formulated as tablets, pills, capsules, liquids, gels, syrups, slurries, suspensions and the like, for oral ingestion by a patient to be treated.

Pharmaceutical compositions suitable for use in the present methods include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The medicaments described herein and which are also for use in the methods provided herein, may include one or more of the following: preserving agents, solubilizing agents, stabilizing agents, wetting agents, emulsifiers, sweeteners, colorants, odorants, salts, buffers, coating agents or antioxidants. They may also contain therapeutically active agents in addition to the compounds and/or agents described herein. Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Pharmaceutical preparations which can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Routes of Administration

Various routes of administration will now be considered in greater detail:

a. Oral Administration

Medicaments adapted for oral administration may be provided as capsules or tablets; as powders or granules; as solutions, syrups or suspensions (in aqueous or non-aqueous liquids); as edible foams or whips; or as emulsions.

Tablets or hard gelatin capsules may comprise lactose, maize starch or derivatives thereof, stearic acid or salts thereof.

Soft gelatin capsules may comprise vegetable oils, waxes, fats, semi-solid, or liquid polyols etc.

Solutions and syrups may comprise water, polyols and sugars. For the preparation of suspensions oils (e.g., vegetable oils) may be used to provide oil-in-water or water-in-oil suspensions.

b. Transdermal Administration

Medicaments adapted for transdermal administration may be provided as discrete patches intended to remain in intimate contact with the epidermis of the recipient for a prolonged period of time. For example, the active ingredient may be delivered from the patch by iontophoresis (Iontophoresis is described in *Pharmaceutical Research*, 3(6):318 (1986)).

c. Topical Administration

Medicaments adapted for topical administration may be provided as ointments, creams, suspensions lotions, powders, solutions, pastes, gels, sprays, aerosols or oils.

For infections of the eye or other external tissues, for example mouth and skin, a topical ointment or cream is preferably used. When formulated in an ointment, the active ingredient may be employed with either a paraffinic or a water-miscible ointment base. Alternatively, the active ingredient may be formulated in a cream with an oil-in-water base or a water-in-oil base.

Medicaments adapted for topical administration to the eye include eye drops. Here the active ingredient can be dissolved or suspended in a suitable carrier, e.g., in an aqueous solvent.

Medicaments adapted for topical administration in the mouth include lozenges, pastilles and mouthwashes.

d. Rectal Administration

Medicaments adapted for rectal administration may be provided as suppositories or enemas.

e. Nasal Administration

Medicaments adapted for nasal administration which use solid carriers include a coarse powder (e.g., having a particle size in the range of 20 to 500 microns). This can be administered in the manner in which snuff is taken, i.e., by rapid inhalation through the nose from a container of powder held close to the nose.

Compositions adopted for nasal administration which use liquid carriers include nasal sprays or nasal drops. These may comprise aqueous or oil solutions of the active ingredient.

Medicaments adapted for administration by inhalation include fine particle dusts or mists, which may be generated by means of various types of apparatus, e.g., pressurized aerosols, nebulizers or insufflators. Such apparatus can be constructed so as to provide predetermined dosages of the active ingredient.

f. Parenteral Administration

Medicaments adapted for parenteral administration include aqueous and non-aqueous sterile injectable solutions or suspensions. These may contain antioxidants, buffers, bacteriostats and solutes which render the compositions substantially isotonic with the blood of an intended recipient. Other components which may be present in such compositions include water, alcohols, polyols, glycerine and vegetable oils, for example. Compositions adapted for parenteral administration may be presented in unit-dose or multi-dose containers, for example sealed ampoules and vials, and may be stored in a freeze-dried (lyophilized) condition requiring only the addition of a sterile liquid carrier, e.g., sterile water for injections, immediately prior to use. Extemporaneous injection solutions and suspensions may be prepared from sterile powders, granules and tablets.

g. Dosages

Dosages will be readily determinable by routine trials, and will be under the control of the physician or clinician. The guiding principle for determining a suitable dose will be delivery of a suitably efficacious but non-toxic, or acceptably toxic, amount of material. (See e.g., Fingl et al., (1975) *The Pharmacological Basis of Therapeutics*, Ch. 1 p. 1). For NN-DNJ or a similar compound, a daily dosage for an adult could be expected to be in the range of from 0.1 mg to 5 g of active agent, and may be in the range of from 3 to 2400 mg, preferably 5 to 800 mg, more preferably 15 to 400 mg, and most preferably 15 to 100 mg. The dosage may be administered in a single daily dose or alternatively in two, three or more doses during the day.

The following examples are proffered merely to illustrate the methods described above; they are not intended to limit in any way the scope of the inventions described herein.

EXAMPLE 1

Inducible p7 Expression in Bacteria

The following set of experiments demonstrate that p7 can be inducibly expressed in bacteria. The experiments may be utilized to determine whether p7 or variants of p7 are capable of permeabilizing membranes. The experiments also show that p7 expression effects a cessation in cell growth, and further, p7 expression effects a release in radioactively labeled uridine.

EXAMPLE 1.1

Materials and Methods

Construction of p7 expression plasmids. Standard cloning procedures were used for construction of the recombinant plasmids by DNA manipulations. The coding region of HCV p7 was amplified by polymerase chain reaction (PCR) using as a template the plasmid pTM1/CE1E2p7 encoding HCV 1a strain cDNA (AF009606), kindly provided by J. Dubuisson. PCR reactions were performed using two oligonucleotide primers:1, AAGCGCCCATGGCTTTGGAGAACC TCGTAATAC (SEQ ID NO.: 2) and 2, ATTGAATTC TTAGTGATGGTGATGGTGATGGTGGTGGTATGCCCG CTGAGGCAAC (SEQ ID NO.: 3). Primers 1 and 2 encode the 5' and 3' terminal region of p7, respectively. To create an NcoI restriction site at the 5' end and an EcoRI restriction site at the 3' end, the underlined sequences were introduced into the primers. The resulting PCR product was purified, digested with NcoI and EcoRI restriction enzymes (Roche), and ligated with pTriEx1.1 expression vector (Novagen), which had been previously digested with NcoI and EcoRI. The ligation mixture was used to transform competent E. coli R. gami (DE3)pLacI cells (CN Biosciences). A bacterial clone containing the recombinant plasmid was amplified in 50 μg/ml carbenicillin (Sigma) containing medium. The plasmid DNA was isolated, subjected to restriction analysis, and sequenced using a primer for the T7 promoter and primer 2, in order to exclude the possibility that mutations had been introduced during the PCR reaction. The isolated p7-containing plasmid was designated pTriEx1.1p7.

Induction of p7 expression in bacteria. Single colonies of E. coli R.gami (DE3)pLacI cells containing either pTriEx1.1 or pTriEx1.1 p7 plasmids were grown in LB medium in the presence of 50 μg/ml carbenicillin by shaking them at 37° C., until they reached an $OD_{600\ nm}$ of 0.5. Three ml of these starter cultures were added to 100 ml of LB medium containing 50 μg/ml carbenicillin and 0.4% glucose, and cells were grown under the same conditions. When the cells reached an $OD_{600\ nm}$ of 0.5-0.7, p7 expression was induced by the addition of 1 mM isopropylthiogalactopyranoside (IPTG) (Roche) and their further growth was followed by monitoring the $OD_{600\ nm}$. Untransformed bacteria (without pTriEx1.1 plasmid) were grown in the absence of carbenicillin.

Release of [$^3$H]-uridine from bacterial cells. Bacteria were grown as described above, but this time in the presence of 2 μCi/ml of [$^3$H]-uridine (Amersham, UK) until they reached an $OD_{600\ nm}$ of 0.5. The cells were then pelletted, washed three times with PBS, and resuspended in 25 ml of growth medium. Fifteen minutes later, p7 expression was induced by the addition of 1 mM IPTG. At various post-induction times, 0.5 ml aliquots were removed, the cells were pelletted by centrifugation, the supernatants were mixed with 3.5 ml of Ultima Gold scintillation cocktail (Packard, UK), and the radioactivity released into the medium was quantified by scintillation counting, using a Beckman LS 3801 scintillation counter.

EXAMPLE 1.1

Results

Inducible p7 expression in bacteria. To evaluate the effect of HCV p7 on membrane permeability, p7 was expressed in E. coil Rosetta gami (DE3)pLacl cells using an IPTG inducible system regulated by the tightly controlled T7lac promoter. (See Dubendorff, J. W. and F. W. Studier, (1991) J. Mol. Biol. 219(1): p. 45-59). Rosetta gami (DE3) pLacl cells carry a chromosomal copy of T7 RNA polymerase under the control of the lacUV5 promoter and supply sufficient lac repressor from the pLacl plasmid to ensure stringent repression in the uninduced state. (See Studier, F. W. and B. A. Moffatt, (1986) J. Mol. Biol. 189(1): p. 113-30). The effect of p7 expression on host cells was followed by monitoring the cell density at various times after induction with IPTG. IPTG addition had no effect on non-transformed cells (FIG. 1A, top panel) and cells transformed with pTriEx1.1 (FIG. 1B, top panel), whereas expression of p7 led to an arrest of cell population growth (FIG. 1C, top panel), most likely due to pore formation in the E. coli cell membranes.

Figure 1:
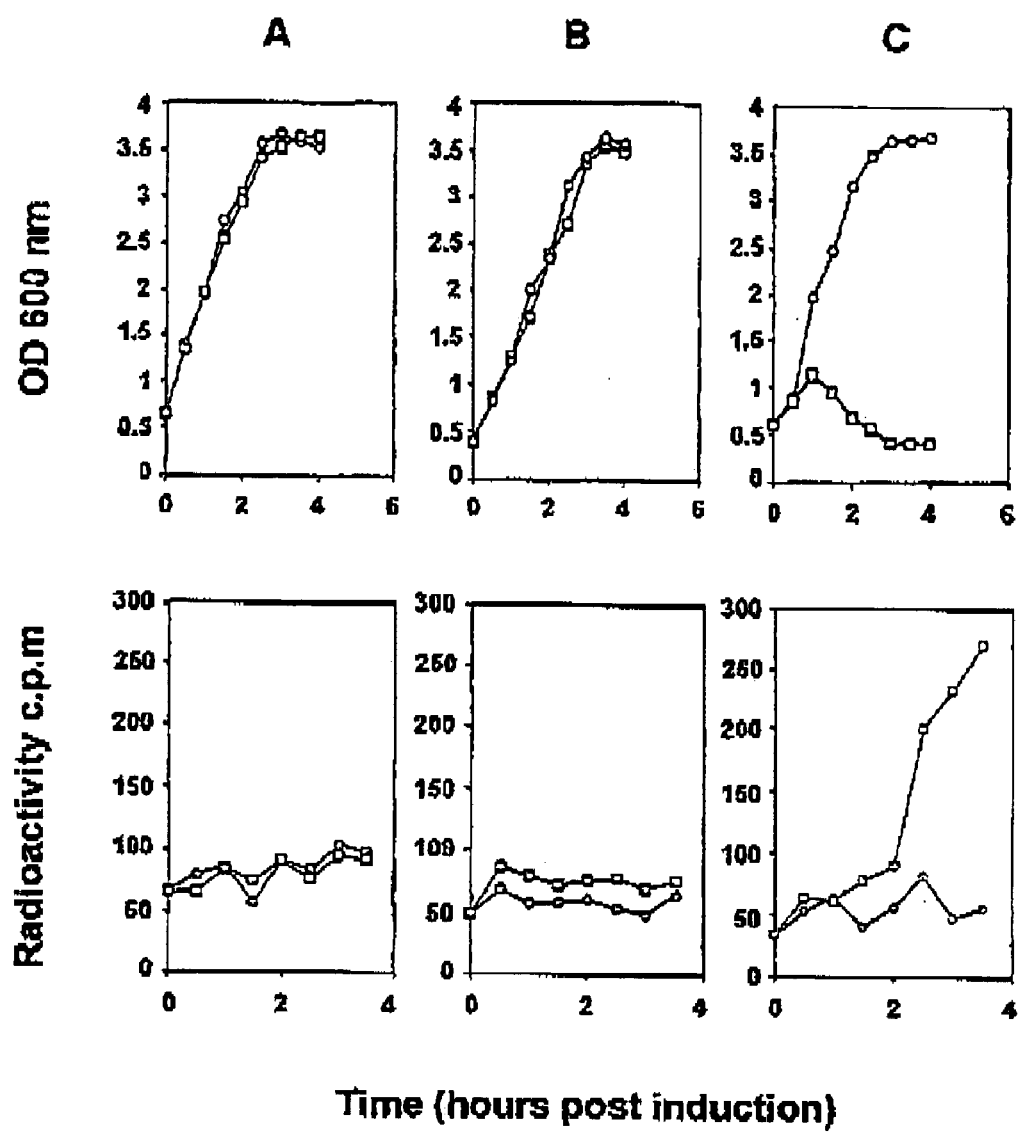

To analyze the efflux of compounds from bacteria expressing HCV p7, recombinant clones were loaded with radioactively labeled uridine, and the release of radioactivity was measured at different time points after induction (FIG. 1, bottom panel). No significant efflux of [$^3$H]-uridine was observed with non-transformed cells or clones carrying the parental plasmid (FIGS. 1A and B, bottom panel). Cells expressing p7 started to release [$^3$H]-uridine into the medium 2 hours after induction of p7 synthesis. Release of [$^3$H]-uridine increased during the 4 hour monitoring period (FIG. 1C), indicating a p7 induced permeability of outer cell membranes.

EXAMPLE 2

Incorporation of Synthesized p7 into BLM

The following sets of experiments demonstrate that synthesized p7 can increase the permeability of BLM as measured by channel recordings. The experiments also show that long alkyl chain iminosugar derivatives inhibit p7 activity.

EXAMPLE 2.1

Materials and Methods

Peptide synthesis and product quality control. Fifty mg of the peptide corresponding to p7 (HCV H strain) with a biotin-tag added at the N-terminus, (biotin-ALENLVIL-NAASLAGTHGLVSLFVFFCFAWYLKGR-WVPGAVYALYGMWPLLLLLLALPQRAYA (SEQ ID NO.: 4)), was synthesized by Albachem, UK. The p7 peptide was analyzed using matrix-assisted laser desorption ionization mass spectrometry (MALDI-MS): The p7 protein was dissolved in 40% acetonitrile to give a solution containing 1 mg/ml peptide. A 1 μl aliquot of this solution was mixed with 1 μl of a solution of a saturated α-cyano-4-hydroxy cinnamic acid in 95:5 acetontirile/water (v/v) containing 16 mM octyl-glucoside solution. An aliquot (1 μl) of this mixture was placed on the mass spectrometer target and allowed to air dry. The detected masses were externally calibrated using a trypsin autodigest. Mass spectra were recorded using a TofSpec 2E mass spectrometer (Micromass, Wythenshawe, Manchester, UK) operating in reflectron mode. The source, extraction, and focusing voltages were 20000, 19950 and 16000V, respectively. All data were analyzed using Mass Lynx version 3.2 software. Following MALDI mass spectrometry analysis, a peak corresponding to the full-length p7 peptide was observed, i.e., at m/z 7247.8.

To measure the purity of the full length peptide, the peptide was further submitted to Tris-Tricine gel electrophoresis, using a modified version of the method developed by Schägger and von Jagow, (1987) Anal. Biochem., 166(2): p. 368-79. Briefly, p7 (5 μg) dissolved in 40% acetonitrile/water (500 μg/ml) was applied in Tricine sample buffer to a gel (8×10 cm$^2$) consisting of a separating gel (20.18% T, 0.83% C), a spacer gel (11.44% T, 0.34% C), and a stacking gel (10.9% T, 0.32% C), with T being the total percentage concentration of both monomers (acrylamide and bisacrylamide) and C being the percentage concentration of the crosslinker relative to T. The gel was run at a constant voltage of 30V until the sample had completely entered the stacking gel, after which the voltage was increased to 110V.

The gels were then analyzed by both silver-staining and Western-blotting. For silver-staining, the gel was washed for 10 min in 50% methanol and for 10 minutes in 5% methanol. The gel was then incubated for 10 min in a 40 μM DTT solution, before it was rinsed with water and incubated in a 0.1% $AgNO_3$ aqueous solution for 10 minutes. It was subsequently washed three times for 10 seconds with water, before the developing solution (7.5 g $NaCO_3$, 125 μl formaldehyde in 250 ml water) was added. The developing process was stopped by the addition of solid citric acid monohydrate. The gel was rinsed with water and soaked in 35% ethanol/2% glycerol before drying.

For Western blot analysis the protein from the gel was transferred in transfer buffer (24 mM Tris base, 192 mM glycine, 20% methanol) to an Immobilon P membrane (Amersham, UK) using a semi-dry electroblotter (2 hours at 40 mA) (Merck). The membrane was blocked overnight in PBS-0.1% Tween containing 3% milk and incubated with horseradish peroxidase-coupled streptavidin (11 μg/ml in PBS-0.1% Tween, 1% milk) for 3 hours at room temperature. It was then washed twice in PBS-0.1% Tween, 1% milk and developed using the ECL detection system (Amersham, UK) following the manufacturer's instructions.

Figure 2:
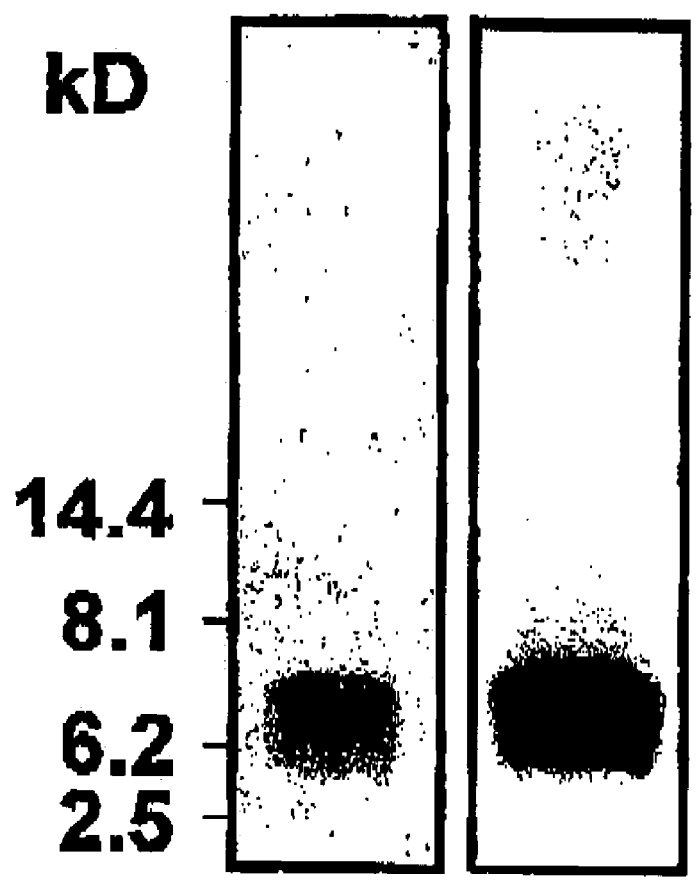

Both the silver-stained gel and the Western-blot revealed one major species of the expected molecular weight (FIG. 2), indicating that at least a portion of the loaded protein contained the full-length, biotinylated p7 protein. However, because differences in resolution between gels with and without urea have been observed before, the chemically synthesized p7 was re-analyzed in the absence of urea. While the streptavidin-probed Western blot revealed the presence of full-length biotinylated p7, an additional broad band of around half the apparent molecular weight was observed on silver-stained gels, which constituted between 50 and 60% of total p7. This broad band may correspond to the smaller non-biotinylated p7 derived species observed by mass spectroscopy, the masses of which theoretically correspond to fragments of p7 containing the N-terminal transmembrane domain. Because the separation of full-length p7 from truncated forms of p7 proved to be difficult, the mixture was subsequently used for channel recordings in black lipid membranes.

Channel recordings in black lipid membranes (BLM). The formation of BLM to study membrane dynamics is well known in the art. A BLM was formed across an elliptical aperture of approximately 100 μm diameter on the long axis in a thin teflon film (with a thickness of approximately 25 μm, Yellow Springs Instruments, Ohio, USA). (See Montal, M. and P. Mueller, (1972) *Proc. Natl. Acad. Sci. USA* 69(12): p. 3561-6. Forty μl of a mixture of lipids (1-palmitoyl-2-oleoyl-sn-glycero-3-phosphoethanolamine (POPE):1-palmitoyl-2-oleoyl-sn-glycero-3-phosphocholine (POPC) (4:1 (w/w)) were dissolved in pentane (5 mg/ml) and spread on top of an aqueous subphase (0.5 M KCl, 5 mM HEPES, 1 mM $CaCl_2$, pH 7.4). This resulted in approximately 0.2 mg of lipid being deposited on each side of the thin teflon film. After a time period of 10 minutes for the solvent to evaporate, the BLM was formed by raising the buffer level in the chambers above the hole in the teflon film. After formation of a stable BLM the HCV p7 protein (dissolved in ethanol) was added from a 200-fold excess stock solution to the aqueous subphase (volume in each chamber on both sides of the bilayer: 2 ml) of the electrically grounded, trans side chamber to reach a final concentration of approximately 50 μM. Recordings appeared after a time delay of approximately 10 minutes. Electrical currents were recorded with an Axopatch 1 D amplifier at a rate of 5 kHz. Data were filtered using a cut off frequency of 50 Hz and further analyzed using the software Origin 5.0. Drugs (from 10 mM stock solutions of NN-DNJ (Synergy Pharmaceuticals), NN-DGJ (Toronto Research Chemicals) and N7-oxanonyl-6-deoxy-DGJ (United Therapeutics Inc.), and from 100 mM stock solutions of NB-DNJ (Sigma) and NB-DGJ were added on either the cis or trans side. Increasing drug concentrations were achieved by sequential addition of equivalent volumes to the measurement chamber. Data was recorded approximately 1 minute after addition of drug for about 3 minutes at +100 mV.

EXAMPLE 2.2

Results

Figure 3:
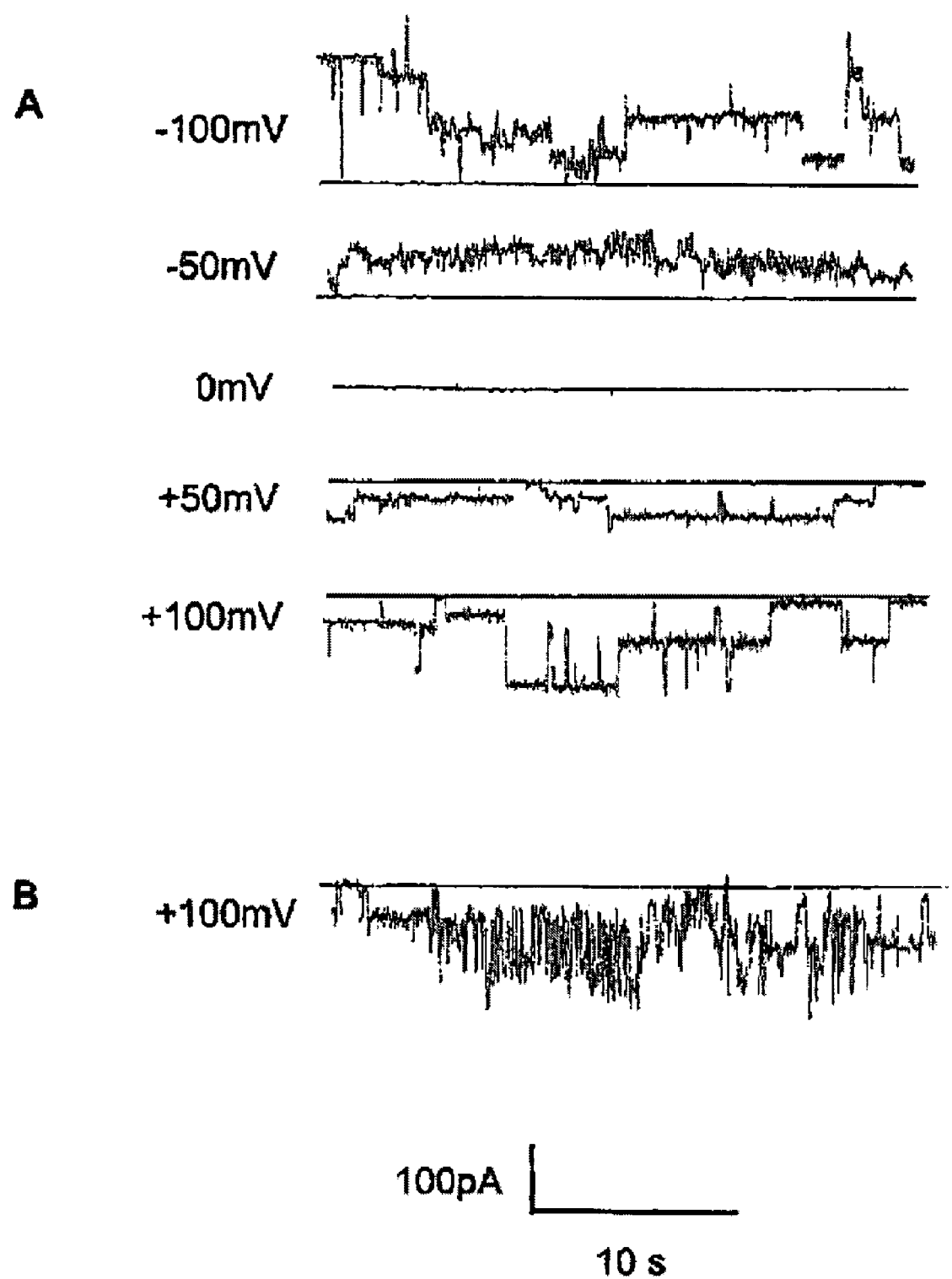
Figure 3:
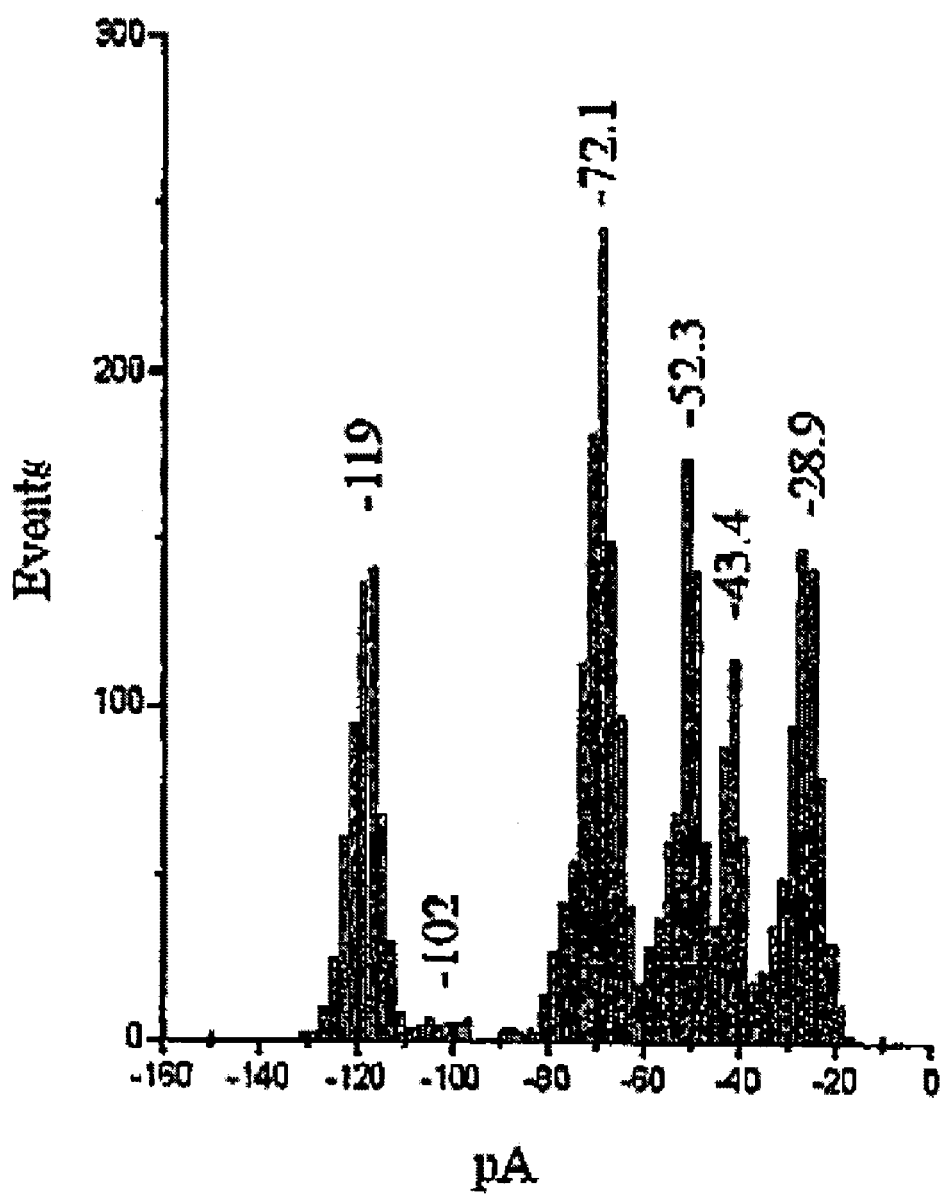

Incorporation of p7 into BLM. Adding p7 to the buffer chamber increases the permeability of BLM, as determined by recording channel signals across the BLM. The channels had a conductance level of up to 2 nS at −100 mV (FIG. 3A). The smallest mean conductance level detected was around 86±22 pS at +50 mV (Table 1).

TABLE 1

Conductance levels of p7. Data are derived from the recordings in FIG. 3A and presented as the mean value ± the standard error of the mean, as shown in brackets. The mean was calculated from 1 second slices of the recordings.

| Applied Voltage (mV) | Conductance (pS) |
| --- | --- |
| +100 | 289 (±19), 383 (±57), 434 (±14), 523 (±14), 629 (±52), 721 (±26), 1025 (±34)*, 1192 (±27) |
| +50 | 86 (+/− 22), 292**, 462 (±26), 614 (±18), 894 (±38) |
| −50 | 1090** |
| −100 | 709 (47)*, 1228 (±38), 1720**, 2000** |

*averaged values from a single section of 1 second with standard deviation
**value as determined from visible inspection of the traces The lifetime of defined conductance levels ranges from hundreds of milliseconds to several seconds. Stable long lasting conductance states differ by about 100 pS (and multiples of it), suggesting the formation of a fairly stable channel with a conductance of around 100 pS. Fluctuation in the recording may indicate the presence of sub-conductance states. An example histogram of recordings taken at +100 mV is shown in FIG. 3B. Prolonged measurements with the same sample result in increasing noise levels, which eventually rule out the assignment of defined conductance levels (FIG. 3C). In some experiments, insertion of p7 into the BLM results in burst-like activity (e.g., FIG. 4, top left panel).

Streptavidin gold staining of membranes that contain biotin-p7 protein and subsequent detection of the complex by transmission electronmicroscopy indicates that the biotin-p7 proteins look like a channel, (data not shown), as reported for biosynthetically-synthesized HCV p7. (See Griffin et al., *FEBS Letters*, 2003, Jan. 20; 535(1-3):34-8). (See also Pavlovic et al., *PNAS* 2003, May 13; 100(10): 6104-8).

Neither a peptide including transmembrane domain I ("TMD I"), (e.g., ALENLVILNAASLAGTGHLVSFV-LFFCFAWYLK (SEQ ID NO.: 5)), nor a peptide including transmembrane domain 11 ("TMD II"), (e.g., GRWVP- GAVYALYGMWPLLLLLLALPQRAYA (SEQ ID NO.: 6)), added to the BLM, were able to form channels on their own as determined by lack of a channel signal. (Data not shown.) Even if both domains were added to the BLM, no channel was formed. (Data not shown.)

Figure 4:
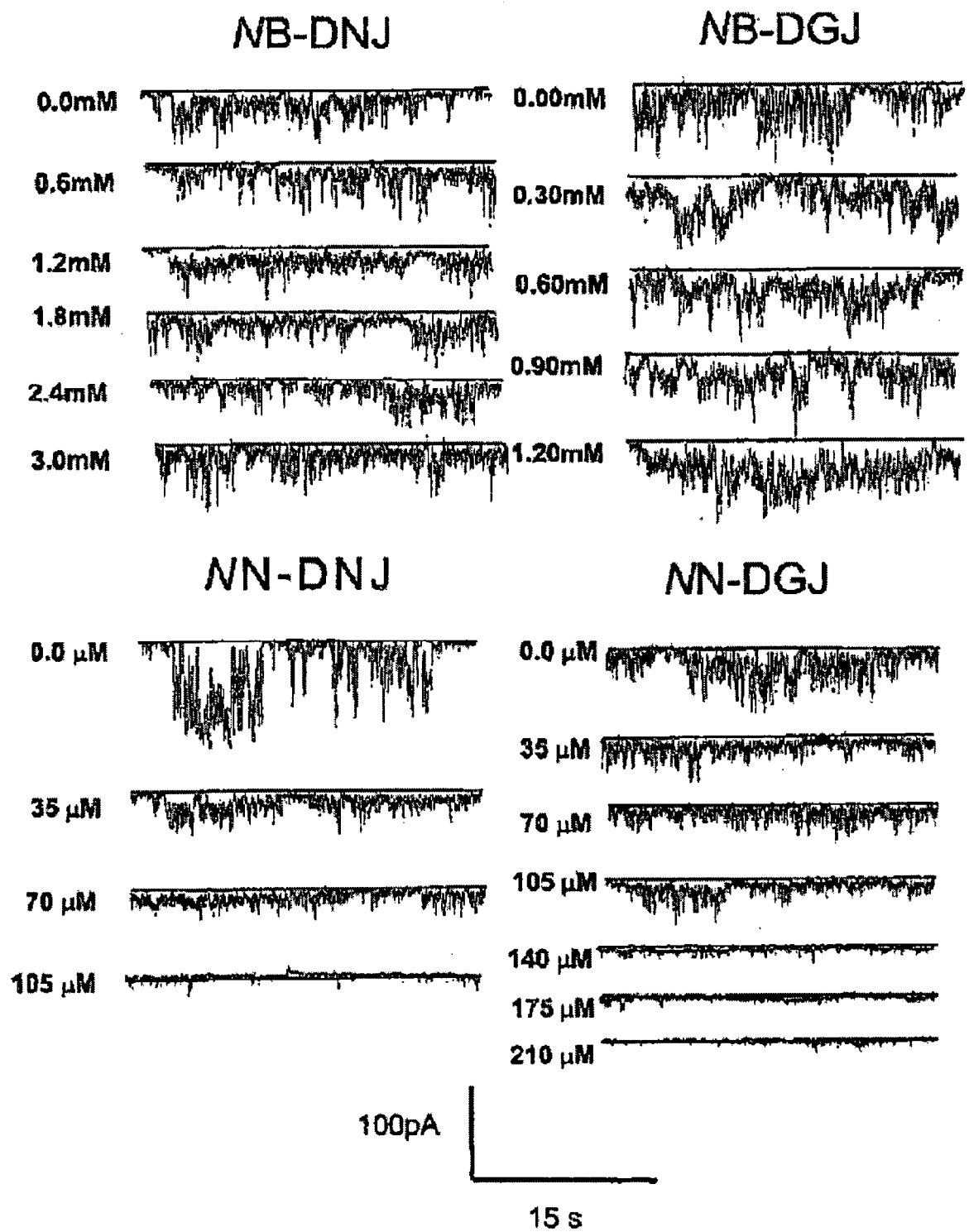
FIG. 4 shows the effect of the short (NB-DNJ, NB-DGJ) and long (NN-DNJ, NN-DGJ) alkylchain iminosugar derivatives on p7 channel signals in BLM. The holding potential was held constant at +100 mV, and the iminosugar derivatives were added to a final concentration as indicated.
Figure 5:
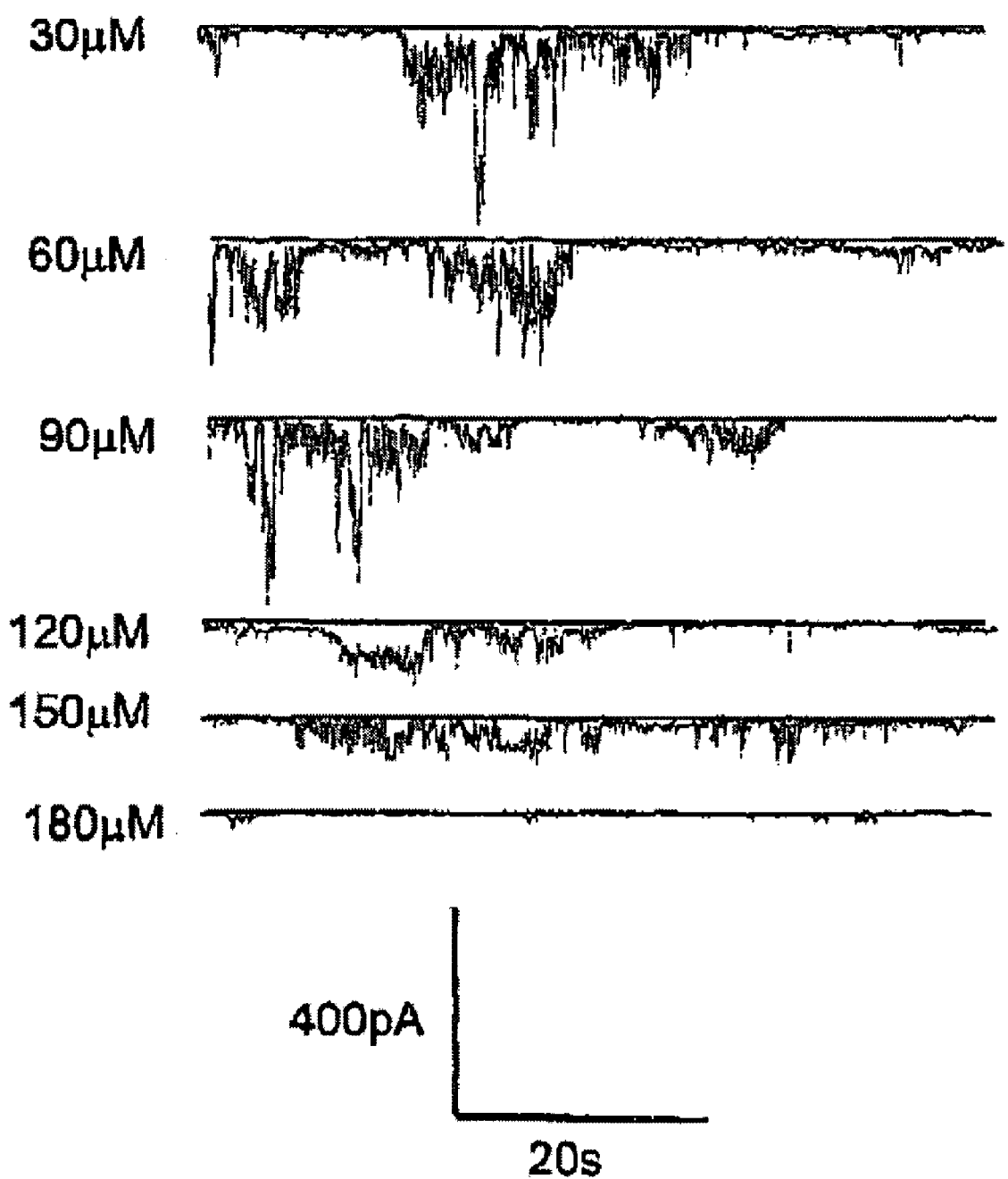
FIG. 5 shows the effect of N7-oxanonyl-6-deoxy-DGJ (alternatively called N7-oxanonyl-methyl-DGJ) on p7 channel signals in BLM. The holding potential was held constant at +100 mV, and N7-oxanonyl-6-deoxy-DGJ was added to a final concentration as indicated.

Increasing drug concentrations of iminosugar derivatives were added to the buffer on one side of the membrane and their effect on p7-induced channel activity was followed. With the short alkylchain derivatives NB-DGJ and NB-DNJ, p7 channel activity remains unchanged (FIG. 4, top panels). Likewise, N-octylglucoside, up to 3.0 mM, had no effect on channel activity. (Data not shown.) However, addition of increasing amounts of the long alkylchain derivatives NN-DGJ, NN-DNJ and N7-oxanonyl-6-deoxy-DGJ led to a dose-dependent inhibition of p7 channel signals (FIG. 4, bottom panels, and FIG. 5). From graphical representations of the resulting integrated normalized current traces and their respective sigmoidal fits (FIG. 6) the approximate binding constants were deduced: $K_{app}$=110.4 (±19.9) μM for NN-DGJ, $K_{app}$=45.2 (±10.7) μM for NN-DNJ, and $K_{app}$=114.2 (±18.3) μM for N7-oxanonyl-6-deoxy-DGJ. Complete blockage of channel activity is observed at about 140 μM for NN-DGJ, 105 μM for NN-DNJ, and 180 μM for N7-oxanonyl-6-deoxy-DGJ. No leak currents were observed with increasing concentrations of any of the drugs.

Similarly, addition of increasing amounts of the long alkylchain derivative, SP240, (i.e., N-10-oxaundecyl-1,6-dideoxygalactonojirimycin), led to a dose-dependent inhibition of p7 channel signals (FIG. 7). Complete blockage of channel activity is observed at about 100 μM for SP240.

All patents and other references cited in the specification are indicative of the level of skill of those skilled in the art to which the inventions pertain, and only those patents and other references cited in the specification as filed are incorporated by reference in their entireties, including any tables and figures, to the same extent as if each reference had been incorporated by reference in its entirety individually.

One skilled in the art would readily appreciate that the present are well adapted to obtain the ends and advantages mentioned, as well as those inherent therein. The methods, variances, and compounds/compositions described herein as presently representative of preferred embodiments are exemplary and are not intended as limitations on the scope of the inventions. Changes therein and other uses will occur to those skilled in the art, which are encompassed within the inventions.

It will be readily apparent to one skilled in the art that varying substitutions and modifications may be made to the inventions disclosed herein without departing from the scope and spirit of the inventions. For example, a variety of different binding pairs can be utilized, as well as a variety of different therapeutic and diagnostic agents. Thus, such additional embodiments are within the scope of the present inventions.

The inventions illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the inventions. Thus, it should be understood that although the present inventions have been specifically disclosed by preferred embodiments and optional features, modification and variation of the concepts herein disclosed may be resorted to by those skilled in the art, and that such modifications and variations are considered to be within the scope of these inventions.

In addition, where features or aspects of the inventions are described in terms of Markush groups or other grouping of alternatives, those skilled in the art will recognize that the inventions are also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described inventions.

---

What is claimed is:

1. A method of screening for an inhibitor of HCV p7 protein, comprising:
   (a) incorporating a full-length HCV p7 protein into a membrane to create an HCV p7-containing membrane, wherein the HCV p7-containing membrane has an increased permeability relative to a membrane that does not contain HCV p7 protein;
   (b) contacting the HCV p7 protein with a test compound;
   (c) comparing the permeability of the HCV p7-containing membrane, wherein the HCV p7 protein has been contacted with a test compound, to the permeability of a HCV p7-containing membrane, wherein the HCV p7 protein has not been contacted with the test compound; and
   (d) observing a decrease in the permeability in the HCV p7-containing membrane, thereby identifying the inhibitor of HCV p7 protein.

2. The method according to claim 1, wherein the HCV p7 protein is selected from a member of HCV clade 1.

3. The method according to claim 1, wherein the HCV p7 protein comprises the amino acid sequence ALENLVILNAASLAGTHGLVSFLVFFCFAWYLKGRVWPGAVYALYGMWPLLLLLLLALPQRAYA (SEQ ID NO.: 1).

4. The method according to claim 1, wherein the HCV p7 protein comprises at least one transmembrane domain and greater than about 70% of total amino acids of the transmembrane domain are members of the group consisting of F, I, W, Y, L, V, M, P, C, and A.

5. The method according to claim 1, wherein the HCV p7 protein is contacted with the test compound when present in the HCV p7-containing membrane.

6. The method according to claim 1, wherein the permeability is compared by recording electrical currents through the membrane.

7. The method according to claim 1, wherein the membrane comprises a black lipid membrane.

8. The method according to claim 1, wherein the test compound inhibits channel formation.

9. The method according to claim 1, wherein the test compound is a channel blocker.

10. The method according to claim 1, wherein the test compound is selected from the group consisting of compounds of formula I or II, related isomers, pharmaceutically acceptable salts, and solvates thereof:

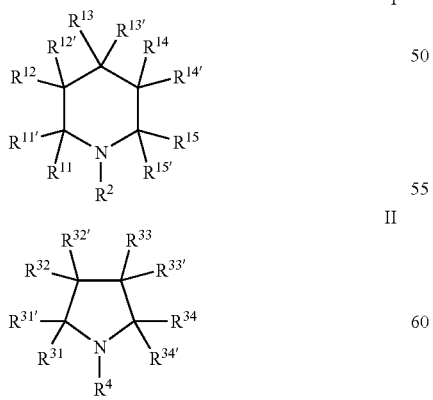

wherein each substituent $R^{11}$, $R^{11'}$, $R^{12}$, $R^{12'}$, $R^{13}$, $R^{13'}$, $R^{14}$, $R^{14'}$, $R^{15}$, $R^{15'}$, $R^{31}$, $R^{31'}$, $R^{32}$, $R^{32'}$, $R^{33}$, $R^{33'}$, $R^{34}$, and $R^{34'}$ is selected, independently from each other, from a group consisting of —H; —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; -(alkylene)oxy(alkyl); —CN; —NO$_2$; —COOH; —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-6}$ alkyl)thio; (C$_{1-6}$ alkyl)sulfonamide; arylsulfonamide; —NHNH$_2$; —NHOH; aryl; and heteroaryl; wherein each substituent may be the same or different;

wherein each alkyl, alkenyl, alkynyl, aryl, and heteroaryl moiety may be optionally substituted with one or more groups independently selected from the group consisting of —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy; aryloxy; aralkoxy; -(alkylene)oxy(alkyl); —CN, —NO$_2$, —COOH, —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-6}$ alkyl)thio; (C$_{1-6}$ alkyl)sulfonamide; arylsulfonamide; —NHNH$_2$; and —NHOH; and $R^2$ and $R^4$ are substituents selected independently of each other from a group consisting of linear $C_{7-18}$ alkyl, substituted $C_{1-18}$ alkyl, branched $C_{3-18}$ alkyl, $C_{2-18}$ alkenyl and alkynyl, and aralkyl;

wherein each linear $C_{7-18}$ alkyl, branched $C_{3-18}$ alkyl, $C_{2-18}$ alkenyl and alkynyl, and aralkyl optionally may be substituted, and each substituted $C_{1-18}$ alkyl is substituted with one or more groups independently selected from a group consisting of —OH; —F; —Cl; —Br; —I; —NH$_2$; alkyl- and dialkylamino; linear or branched $C_{1-6}$ alkyl, $C_{2-6}$ alkenyl and alkynyl; aralkyl; linear or branched $C_{1-6}$ alkoxy, aryloxy; aralkoxy; —CN, —NO$_2$, —COOH, —COO(alkyl); —COO(aryl); —C(O)NH(C$_{1-6}$ alkyl); —C(O)NH(aryl); sulfonyl; (C$_{1-6}$ alkyl)sulfonyl; arylsulfonyl; sulfamoyl, (C$_{1-6}$ alkyl)sulfamoyl; (C$_{1-6}$ alkyl)thio; (C$_{1-6}$ alkyl)sulfonamide; arylsulfonamide; —NHNH$_2$; and —NHOH.

11. The method according to claim 1, wherein the test compound is amantadine or a derivative thereof.

12. A method of screening for an inhibitor of HCV p7 protein, comprising:
   (a) incorporating a biotinylated full-length HCV p7 protein into a membrane to create an HCV p7-containing membrane, wherein the HCV p7-containing membrane has an increased permeability relative to a membrane that does not contain HCV p7 protein;
   (b) contacting the HCV p7 protein with a test compound;
   (c) comparing the permeability of the HCV p7-containing membrane, wherein the HCV p7 protein has been contacted with the test compound, to the permeability of a HCV p7-containing membrane, wherein the HCV p7 protein has not been contacted with the test compound; and
   (d) observing a decrease in the permeability in the HCV p7-containing membrane, thereby identifying the inhibitor of HCV p7 protein.

13. The method according to claim 12, wherein the biotinylated HCV p7 protein comprises the amino acid sequence ALENLVILNAASLAGTHGLVSFLVFFCFAWYLKGRVWPGAVYALYGMWPLLLLLLALPQRAYA (SEQ ID NO.: 1).

14. The method according to claim 12, wherein the biotinylated HCV p7 protein comprises at least one transmembrane domain and greater than about 70% of total amino acids of the transmembrane domain are members of the group consisting of F, I, W, Y, L, V, M, P, C, and A.

15. The method according to claim 12, wherein the biotinylated HCV p7 protein is contacted with the test compound when present in the HCV p7-containing membrane.

16. The method according to claim 12, wherein the permeability is compared by recording electrical currents through the membrane.

17. The method according to claim 12, wherein the membrane comprises a black lipid membrane.

18. The method according to claim 12, wherein the test compound inhibits channel formation.

19. The method according to claim 12, wherein the test compound is a channel blocker.

* * * * *